United States Patent
Buchbinder et al.

(10) Patent No.: US 8,366,706 B2
(45) Date of Patent: Feb. 5, 2013

(54) SYSTEMS AND METHODS FOR PUNCTURE CLOSURE

(75) Inventors: Maurice Buchbinder, La Jolla, CA (US); Amnon Yadin, Kfar Vitkin (IL); Noam Mizrahi, Kfar Vitkin (IL); Shimon Eckhouse, Haifa (IL); Eran Goldberg, Nesher (IL); Aharon Cohen, Zichron Yaakov (IL); Julie Logan, La Jolla, CA (US)

(73) Assignee: Cardiodex, Ltd., Cesarea (IL)

( * ) Notice: Subject to any disclaimer, the term of this patent is extended or adjusted under 35 U.S.C. 154(b) by 1089 days.

(21) Appl. No.: 12/192,911

(22) Filed: Aug. 15, 2008

(65) Prior Publication Data

US 2009/0125056 A1    May 14, 2009

Related U.S. Application Data

(60) Provisional application No. 60/935,484, filed on Aug. 15, 2007, provisional application No. 60/960,604, filed on Oct. 5, 2007, provisional application No. 61/006,926, filed on Feb. 6, 2008.

(51) Int. Cl.
*A61B 18/04* (2006.01)

(52) U.S. Cl. ............................. 606/27; 606/28; 606/213

(58) Field of Classification Search .................. None
See application file for complete search history.

(56) References Cited

U.S. PATENT DOCUMENTS

| | | | |
|---|---|---|---|
| 524,417 A | 8/1894 | Fahey | |
| 1,596,004 A | 8/1926 | De Bengoa | |
| 1,731,069 A | 10/1929 | Herman | |
| 1,881,250 A | 10/1932 | Tomlinson | |
| 1,983,669 A | 12/1934 | Kimble | |
| 2,144,090 A | 1/1939 | Trice | |
| 2,790,442 A | 4/1957 | Donaldson | |
| 2,808,833 A | 10/1957 | August | |
| 3,100,489 A | 8/1963 | Bagley | |
| 3,176,114 A | 3/1965 | Kneisley | |
| 3,301,258 A | 1/1967 | Werner et al. | |
| 3,302,635 A | 2/1967 | Pittman | |
| 3,494,364 A | 2/1970 | Peters | |

(Continued)

FOREIGN PATENT DOCUMENTS

| | | |
|---|---|---|
| BR | 0208039 | 1/2006 |
| BR | PI0208039-7 A | 1/2006 |

(Continued)

OTHER PUBLICATIONS

U.S. Appl. No. 60/630,245, filed Nov. 22, 2004, Mizrahi et al.

(Continued)

*Primary Examiner* — Corrine M McDermott
*Assistant Examiner* — Todd J Scherbel
(74) *Attorney, Agent, or Firm* — Venable LLP

(57) ABSTRACT

Systems, apparatuses and methods are provided for use in closing punctures in vessel walls. An apparatus may have various combinations of an anchoring device, a positioning device and a heating element for closing a puncture within a vessel wall. An anchoring device may be a balloon, an expansible cage, a wire operated T-anchor, and/or a floating anchor. A positioning device may be a balloon, a sponge, and/or an expansible cage. A heating element may be flexible or rigid and preferably provides heat to target tissue through conduction and convection. A heating element may be flat-ended or dome-shaped. The heating element and anchoring device may be positioned a fixed distance apart to sandwich tissue between the heating element and the anchoring device. The heating element may operate in multiple stages. An initial stage may non-permanently adhere the heating element to the tissue and the subsequent stage may close the puncture.

16 Claims, 37 Drawing Sheets

U.S. PATENT DOCUMENTS

| | | |
|---|---|---|
| 3,500,828 A | 3/1970 | Podhora |
| 3,532,095 A | 10/1970 | Miller |
| 3,595,238 A | 7/1971 | Gavrilov et al. |
| 3,613,682 A | 10/1971 | Naylor |
| 3,636,943 A | 1/1972 | Balamuth |
| 3,699,967 A | 10/1972 | Anderson |
| 3,794,040 A | 2/1974 | Balamuth |
| 3,801,766 A | 4/1974 | Morrison, Jr. |
| 3,801,800 A | 4/1974 | Newton |
| 3,825,004 A | 7/1974 | Durden, III |
| 3,858,586 A | 1/1975 | Lessen |
| 3,874,388 A | 4/1975 | King et al. |
| 3,886,944 A | 6/1975 | Jamshidi |
| 3,920,021 A | 11/1975 | Hiltebrandt |
| 3,929,137 A | 12/1975 | Gonser |
| 3,938,527 A | 2/1976 | Rioux et al. |
| 3,963,030 A | 6/1976 | Newton |
| 3,978,863 A | 9/1976 | Fettel et al. |
| 3,980,085 A | 9/1976 | Ikuno |
| 4,003,380 A | 1/1977 | Wien |
| 4,007,743 A | 2/1977 | Blake |
| 4,011,872 A | 3/1977 | Komiya |
| 4,014,343 A | 3/1977 | Esty |
| 4,016,881 A | 4/1977 | Rioux et al. |
| 4,043,342 A | 8/1977 | Morrison, Jr. |
| 4,051,855 A | 10/1977 | Schneiderman |
| 4,054,143 A | 10/1977 | Bauer |
| 4,074,718 A | 2/1978 | Morrison, Jr. |
| 4,112,950 A | 9/1978 | Pike |
| 4,122,853 A | 10/1978 | Smith |
| 4,162,673 A | 7/1979 | Patel |
| 4,168,708 A | 9/1979 | Lepley, Jr. et al. |
| 4,198,957 A | 4/1980 | Cage et al. |
| 4,202,337 A | 5/1980 | Hren et al. |
| 4,211,230 A | 7/1980 | Woltosz |
| 4,215,699 A | 8/1980 | Patel |
| 4,228,800 A | 10/1980 | Degler, Jr. et al. |
| 4,230,119 A | 10/1980 | Blum |
| 4,269,174 A | 5/1981 | Adair |
| 4,271,839 A | 6/1981 | Fogarty et al. |
| 4,271,847 A | 6/1981 | Stokes |
| 4,273,127 A | 6/1981 | Auth et al. |
| 4,303,073 A | 12/1981 | Archibald |
| 4,314,555 A | 2/1982 | Sagae |
| 4,314,559 A | 2/1982 | Allen |
| 4,317,445 A | 3/1982 | Robinson |
| 4,327,709 A | 5/1982 | Hanson et al. |
| 4,352,924 A | 10/1982 | Wooten et al. |
| 4,353,371 A | 10/1982 | Cosman |
| 4,359,052 A | 11/1982 | Staub |
| 4,364,392 A | 12/1982 | Strother et al. |
| 4,370,980 A | 2/1983 | Lottick |
| 4,390,018 A | 6/1983 | Zukowski |
| 4,404,971 A | 9/1983 | LeVeen et al. |
| 4,411,266 A | 10/1983 | Cosman |
| 4,418,692 A | 12/1983 | Guay |
| 4,424,833 A | 1/1984 | Spector et al. |
| 4,470,415 A | 9/1984 | Wozniak |
| 4,476,862 A | 10/1984 | Pao |
| 4,481,057 A | 11/1984 | Beard |
| 4,483,338 A | 11/1984 | Bloom et al. |
| 4,492,231 A | 1/1985 | Auth |
| 4,498,475 A | 2/1985 | Schneiderman |
| 4,520,823 A | 6/1985 | LeVeen et al. |
| 4,522,205 A | 6/1985 | Taylor et al. |
| 4,532,924 A | 8/1985 | Auth et al. |
| 4,539,987 A | 9/1985 | Nath et al. |
| 4,548,207 A | 10/1985 | Reimels |
| 4,625,724 A | 12/1986 | Suzuki et al. |
| 4,637,392 A | 1/1987 | Sorochenko |
| 4,645,491 A | 2/1987 | Evans |
| 4,654,024 A | 3/1987 | Crittenden et al. |
| 4,671,274 A | 6/1987 | Sorochenko |
| 4,672,969 A | 6/1987 | Dew |
| 4,682,596 A | 7/1987 | Bales et al. |
| 4,708,136 A | 11/1987 | Saito |
| 4,709,698 A | 12/1987 | Johnston et al. |
| 4,716,897 A | 1/1988 | Noguchi et al. |
| 4,717,381 A | 1/1988 | Papantonakos |
| 4,735,201 A | 4/1988 | O'Reilly |
| 4,744,359 A | 5/1988 | Hatta et al. |
| 4,744,364 A | 5/1988 | Kensey |
| 4,760,847 A | 8/1988 | Vaillancourt |
| 4,765,331 A | 8/1988 | Petruzzi et al. |
| 4,776,349 A | 10/1988 | Nashef et al. |
| 4,790,819 A | 12/1988 | Li et al. |
| 4,801,293 A | 1/1989 | Jackson |
| 4,832,688 A | 5/1989 | Sagae et al. |
| 4,834,725 A | 5/1989 | Iwatschenko |
| 4,836,204 A | 6/1989 | Landymore et al. |
| 4,848,337 A | 7/1989 | Shaw et al. |
| 4,848,339 A | 7/1989 | Rink et al. |
| 4,848,352 A | 7/1989 | Pohndorf et al. |
| 4,850,960 A | 7/1989 | Grayzel |
| 4,852,568 A | 8/1989 | Kensey |
| 4,854,320 A | 8/1989 | Dew et al. |
| 4,860,745 A | 8/1989 | Farin et al. |
| 4,869,248 A | 9/1989 | Narula |
| 4,890,612 A | 1/1990 | Kensey |
| 4,900,303 A | 2/1990 | Lemelson |
| 4,917,089 A | 4/1990 | Sideris |
| 4,920,980 A | 5/1990 | Jackowski |
| 4,921,478 A | 5/1990 | Solano et al. |
| 4,929,246 A | 5/1990 | Sinofsky |
| 4,938,761 A | 7/1990 | Ensslin |
| 4,943,290 A | 7/1990 | Rexroth et al. |
| 4,946,463 A | 8/1990 | Wright |
| 4,953,559 A | 9/1990 | Salerno |
| 4,960,133 A | 10/1990 | Hewson |
| 4,961,729 A | 10/1990 | Vaillancourt |
| 4,979,948 A | 12/1990 | Geddes et al. |
| 4,994,060 A | 2/1991 | Rink et al. |
| 5,002,051 A | 3/1991 | Dew et al. |
| 5,006,119 A | 4/1991 | Acker et al. |
| 5,009,656 A | 4/1991 | Reimels |
| 5,013,312 A | 5/1991 | Parins et al. |
| 5,021,059 A | 6/1991 | Kensey et al. |
| 5,035,695 A | 7/1991 | Weber, Jr. et al. |
| 5,038,789 A | 8/1991 | Frazin |
| 5,047,025 A | 9/1991 | Taylor et al. |
| 5,047,028 A | 9/1991 | Qian |
| 5,049,148 A | 9/1991 | Mehl |
| 5,053,046 A | 10/1991 | Janese |
| 5,057,105 A | 10/1991 | Malone et al. |
| 5,061,267 A | 10/1991 | Zeiher |
| 5,061,274 A | 10/1991 | Kensey |
| 5,073,166 A | 12/1991 | Parks et al. |
| 5,078,743 A | 1/1992 | Mikalov et al. |
| 5,080,660 A | 1/1992 | Buelna |
| 5,085,659 A | 2/1992 | Rydell |
| 5,087,256 A | 2/1992 | Taylor et al. |
| 5,088,997 A | 2/1992 | Delahuerga et al. |
| 5,103,804 A | 4/1992 | Abele et al. |
| 5,108,392 A | 4/1992 | Spingler |
| 5,108,420 A | 4/1992 | Marks |
| 5,108,421 A | 4/1992 | Fowler |
| RE33,925 E | 5/1992 | Bales et al. |
| 5,116,332 A | 5/1992 | Lottick |
| 5,122,137 A | 6/1992 | Lennox |
| 5,122,139 A | 6/1992 | Sutter |
| 5,129,882 A | 7/1992 | Weldon et al. |
| 5,131,394 A | 7/1992 | Gehlbach |
| 5,133,714 A | 7/1992 | Beane |
| 5,141,515 A | 8/1992 | Eberbach |
| 5,147,316 A | 9/1992 | Castillenti |
| 5,147,357 A | 9/1992 | Rose et al. |
| 5,151,098 A | 9/1992 | Loertscher |
| 5,151,102 A | 9/1992 | Kamiyama et al. |
| 5,156,613 A | 10/1992 | Sawyer |
| 5,158,561 A | 10/1992 | Rydell et al. |
| 5,159,925 A | 11/1992 | Neuwirth et al. |
| 5,178,620 A | 1/1993 | Eggers et al. |
| 5,183,464 A | 2/1993 | Dubrul et al. |
| 5,188,602 A * | 2/1993 | Nichols ............ 604/113 |
| 5,188,634 A | 2/1993 | Hussein et al. |
| 5,190,541 A | 3/1993 | Abele et al. |
| 5,192,300 A | 3/1993 | Fowler |

| | | | | | |
|---|---|---|---|---|---|
| 5,192,302 A | 3/1993 | Kensey et al. | 5,895,386 A | 4/1999 | Odell et al. |
| 5,207,675 A | 5/1993 | Canady | 5,906,636 A | 5/1999 | Casscells, III et al. |
| 5,211,624 A | 5/1993 | Cinberg et al. | 5,911,719 A | 6/1999 | Eggers |
| 5,215,103 A | 6/1993 | Desai | 5,922,009 A | 7/1999 | Epstein et al. |
| 5,217,024 A | 6/1993 | Dorsey et al. | 5,928,266 A | 7/1999 | Kontos |
| 5,217,451 A | 6/1993 | Freitas | 5,941,897 A | 8/1999 | Myers |
| 5,217,458 A | 6/1993 | Parins | 5,944,730 A | 8/1999 | Nobles et al. |
| 5,217,459 A | 6/1993 | Kamerling | 5,951,589 A | 9/1999 | Epstein et al. |
| 5,217,460 A | 6/1993 | Knoepfler | 5,964,782 A | 10/1999 | Lafontaine et al. |
| 5,220,924 A | 6/1993 | Frazin | 5,984,950 A | 11/1999 | Cragg et al. |
| 5,221,259 A | 6/1993 | Weldon et al. | 6,002,361 A | 12/1999 | Schipper |
| 5,221,281 A | 6/1993 | Klicek | 6,007,563 A | 12/1999 | Nash et al. |
| 5,222,974 A | 6/1993 | Kensey et al. | 6,022,336 A | 2/2000 | Zadno-Azizi et al. |
| 5,226,908 A | 7/1993 | Yoon | 6,022,361 A | 2/2000 | Epstein et al. |
| 5,230,349 A | 7/1993 | Langberg | 6,033,398 A | 3/2000 | Farley et al. |
| 5,257,635 A | 11/1993 | Langberg | 6,033,401 A | 3/2000 | Edwards et al. |
| 5,258,000 A | 11/1993 | Gianturco | 6,045,569 A | 4/2000 | Kensey et al. |
| 5,258,006 A | 11/1993 | Rydell et al. | 6,048,358 A | 4/2000 | Barak |
| 5,269,780 A | 12/1993 | Roos | 6,056,768 A | 5/2000 | Cates et al. |
| 5,275,616 A | 1/1994 | Fowler | 6,056,769 A | 5/2000 | Epstein et al. |
| 5,277,696 A | 1/1994 | Hagen | 6,063,085 A * | 5/2000 | Tay et al. .................. 606/50 |
| 5,281,216 A | 1/1994 | Klicek | 6,071,277 A | 6/2000 | Farley et al. |
| 5,282,799 A | 2/1994 | Rydell | 6,071,300 A | 6/2000 | Brenneman et al. |
| 5,282,827 A | 2/1994 | Kensey et al. | 6,080,183 A | 6/2000 | Tsugita et al. |
| 5,290,310 A | 3/1994 | Makower et al. | 6,090,130 A | 7/2000 | Nash et al. |
| 5,292,332 A | 3/1994 | Lee | 6,104,291 A | 8/2000 | Beauvillier et al. |
| 5,304,117 A | 4/1994 | Wilk | 6,111,424 A | 8/2000 | Bosacchi |
| 5,304,214 A | 4/1994 | DeFord et al. | 6,113,598 A | 9/2000 | Baker |
| 5,306,254 A | 4/1994 | Nash et al. | 6,120,524 A | 9/2000 | Taheri |
| 5,320,639 A | 6/1994 | Rudnick | 6,126,635 A | 10/2000 | Simpson et al. |
| 5,324,306 A | 6/1994 | Makower et al. | 6,142,994 A | 11/2000 | Swanson et al. |
| 5,342,359 A | 8/1994 | Rydell | 6,152,920 A | 11/2000 | Thompson et al. |
| 5,342,393 A | 8/1994 | Stack | 6,179,832 B1 | 1/2001 | Jones et al. |
| 5,349,166 A | 9/1994 | Taylor | 6,179,863 B1 | 1/2001 | Kensey et al. |
| 5,364,389 A | 11/1994 | Anderson | 6,217,574 B1 | 4/2001 | Webster |
| 5,370,660 A | 12/1994 | Weinstein et al. | 6,228,082 B1 | 5/2001 | Baker et al. |
| 5,383,896 A | 1/1995 | Gershony et al. | 6,235,027 B1 | 5/2001 | Herzon |
| 5,383,899 A | 1/1995 | Hammerslag | 6,267,758 B1 | 7/2001 | Daw et al. |
| 5,411,520 A | 5/1995 | Nash et al. | 6,287,322 B1 | 9/2001 | Zhu et al. |
| 5,413,571 A | 5/1995 | Katsaros et al. | 6,306,133 B1 | 10/2001 | Tu et al. |
| 5,415,657 A | 5/1995 | Taymor-Luria | 6,315,787 B1 | 11/2001 | Tsugita et al. |
| 5,417,689 A | 5/1995 | Fine | 6,322,559 B1 | 11/2001 | Daulton et al. |
| 5,419,195 A | 5/1995 | Quinn | 6,350,274 B1 | 2/2002 | Li |
| 5,419,765 A | 5/1995 | Weldon et al. | 6,352,533 B1 | 3/2002 | Ellman et al. |
| 5,431,639 A | 7/1995 | Shaw | 6,368,341 B1 | 4/2002 | Abrahamson |
| 5,437,631 A | 8/1995 | Janzen | 6,371,964 B1 | 4/2002 | Vargas et al. |
| 5,441,517 A | 8/1995 | Kensey et al. | 6,371,974 B1 | 4/2002 | Brenneman et al. |
| 5,454,833 A | 10/1995 | Boussignac et al. | 6,398,780 B1 | 6/2002 | Farley et al. |
| 5,458,573 A | 10/1995 | Summers | 6,398,782 B1 | 6/2002 | Pecor et al. |
| 5,486,195 A | 1/1996 | Myers et al. | 6,402,745 B1 | 6/2002 | Wilk |
| 5,507,744 A | 4/1996 | Tay et al. | 6,409,739 B1 | 6/2002 | Nobles et al. |
| 5,540,715 A | 7/1996 | Katsaros et al. | 6,443,947 B1 | 9/2002 | Marko et al. |
| RE35,330 E | 9/1996 | Malone et al. | 6,450,989 B2 | 9/2002 | Dubrul et al. |
| 5,593,406 A | 1/1997 | Eggers et al. | 6,451,007 B1 | 9/2002 | Koop et al. |
| 5,611,798 A | 3/1997 | Eggers | 6,468,272 B1 | 10/2002 | Koblish et al. |
| 5,624,452 A | 4/1997 | Yates | 6,482,179 B1 | 11/2002 | Chu et al. |
| 5,626,601 A | 5/1997 | Gershony et al. | 6,503,247 B2 | 1/2003 | Swartz et al. |
| 5,630,833 A | 5/1997 | Katsaros et al. | 6,508,828 B1 | 1/2003 | Akerfeldt et al. |
| 5,645,566 A | 7/1997 | Brenneman et al. | 6,511,479 B2 | 1/2003 | Gentelia et al. |
| 5,654,566 A | 8/1997 | Johnson | 6,512,458 B1 | 1/2003 | Kobayashi et al. |
| 5,676,689 A | 10/1997 | Kensey et al. | 6,529,756 B1 | 3/2003 | Phan et al. |
| 5,700,277 A | 12/1997 | Nash et al. | 6,533,778 B2 | 3/2003 | Herzon |
| 5,702,387 A | 12/1997 | Arts et al. | 6,537,299 B1 | 3/2003 | Hogendijk et al. |
| 5,716,325 A | 2/1998 | Bonutti | 6,551,313 B1 | 4/2003 | Levin |
| 5,716,375 A | 2/1998 | Fowler | 6,569,161 B2 | 5/2003 | Zappala |
| RE35,755 E | 3/1998 | Qian | 6,569,182 B1 | 5/2003 | Balceta et al. |
| 5,725,551 A | 3/1998 | Myers et al. | 6,589,237 B2 | 7/2003 | Woloszko et al. |
| 5,728,122 A | 3/1998 | Leschinsky et al. | 6,593,853 B1 | 7/2003 | Barrett et al. |
| 5,728,133 A | 3/1998 | Kontos | 6,626,899 B2 | 9/2003 | Houser et al. |
| 5,728,134 A | 3/1998 | Barak | 6,626,901 B1 | 9/2003 | Treat et al. |
| 5,746,755 A | 5/1998 | Wood et al. | 6,656,136 B1 | 12/2003 | Weng et al. |
| 5,782,860 A | 7/1998 | Epstein et al. | 6,656,207 B2 | 12/2003 | Epstein et al. |
| 5,782,861 A | 7/1998 | Cragg et al. | 6,657,447 B1 | 12/2003 | Parandoosh |
| 5,810,810 A | 9/1998 | Tay et al. | 6,676,657 B2 | 1/2004 | Wood |
| 5,836,945 A | 11/1998 | Perkins | 6,676,685 B2 | 1/2004 | Pedros et al. |
| 5,853,421 A | 12/1998 | Leschinsky et al. | 6,679,904 B2 | 1/2004 | Gleeson et al. |
| 5,868,778 A | 2/1999 | Gershony et al. | 6,682,526 B1 | 1/2004 | Jones et al. |
| 5,879,499 A | 3/1999 | Corvi | 6,689,126 B1 | 2/2004 | Farley et al. |
| 5,891,138 A | 4/1999 | Tu et al. | 6,699,262 B2 | 3/2004 | Redmond et al. |

| | | |
|---|---|---|
| 6,712,804 B2 | 3/2004 | Roue et al. |
| 6,712,806 B2 | 3/2004 | St. Germain et al. |
| 6,712,815 B2 | 3/2004 | Sampson et al. |
| 6,743,195 B2 | 6/2004 | Zucker |
| 6,768,086 B2 | 7/2004 | Sullivan et al. |
| 6,772,013 B1 | 8/2004 | Ingle et al. |
| 6,780,177 B2 | 8/2004 | Shafirstein et al. |
| 6,814,743 B2 | 11/2004 | Chin et al. |
| 6,817,743 B2 | 11/2004 | Sharper |
| 6,840,666 B2 | 1/2005 | Enachescu et al. |
| 6,846,321 B2 | 1/2005 | Zucker |
| 6,860,880 B2 | 3/2005 | Treat et al. |
| 6,904,303 B2 * | 6/2005 | Phan et al. ............ 600/374 |
| 6,908,463 B2 | 6/2005 | Treat et al. |
| 6,932,810 B2 * | 8/2005 | Ryan .................. 606/38 |
| 6,939,363 B2 | 9/2005 | Åkerfeldt |
| 6,942,674 B2 | 9/2005 | Belef et al. |
| 6,960,206 B2 | 11/2005 | Keane |
| 6,969,397 B2 | 11/2005 | Ginn |
| 6,984,219 B2 | 1/2006 | Ashby et al. |
| 6,997,926 B2 | 2/2006 | Gellman et al. |
| 7,001,398 B2 | 2/2006 | Carley et al. |
| 7,008,441 B2 | 3/2006 | Zucker |
| 7,025,748 B2 | 4/2006 | Ashby |
| 7,029,489 B1 | 4/2006 | Ashby et al. |
| 7,033,352 B1 | 4/2006 | Gauthier et al. |
| 7,037,322 B1 | 5/2006 | Sing et al. |
| 7,070,597 B2 | 7/2006 | Truckai et al. |
| 7,073,509 B2 | 7/2006 | Tenerz et al. |
| 7,099,717 B2 | 8/2006 | Woodard et al. |
| 7,115,127 B2 | 10/2006 | Lindenbaum et al. |
| 7,144,411 B2 | 12/2006 | Ginn et al. |
| 7,147,634 B2 | 12/2006 | Nesbitt |
| 7,151,442 B1 | 12/2006 | Nguyen |
| 7,153,301 B2 | 12/2006 | Swartz et al. |
| 7,154,283 B1 | 12/2006 | Weakley et al. |
| 7,160,297 B2 | 1/2007 | Nesbitt |
| 7,164,353 B2 | 1/2007 | Puleston et al. |
| 7,175,646 B2 | 2/2007 | Brenneman et al. |
| 7,184,811 B2 | 2/2007 | Phan et al. |
| 7,201,725 B1 | 4/2007 | Cragg et al. |
| 7,211,080 B2 | 5/2007 | Treat et al. |
| 7,223,266 B2 | 5/2007 | Lindenbaum et al. |
| 7,225,992 B2 | 6/2007 | Forster |
| 7,257,450 B2 | 8/2007 | Auth et al. |
| 7,474,909 B2 | 1/2009 | Phan et al. |
| 7,850,685 B2 * | 12/2010 | Kunis et al. ............ 606/41 |
| 2001/0003158 A1 | 6/2001 | Kensey et al. |
| 2001/0007070 A1 | 7/2001 | Stewart et al. |
| 2001/0029373 A1 | 10/2001 | Baker et al. |
| 2002/0002371 A1 * | 1/2002 | Acker et al. ............ 606/27 |
| 2002/0022822 A1 | 2/2002 | Cragg et al. |
| 2002/0062130 A1 | 5/2002 | Jugenheimer et al. |
| 2002/0072761 A1 | 6/2002 | Abrams et al. |
| 2002/0133123 A1 | 9/2002 | Zucker |
| 2002/0156495 A1 | 10/2002 | Brenneman et al. |
| 2002/0193808 A1 | 12/2002 | Belef et al. |
| 2003/0005397 A1 | 1/2003 | Larsen |
| 2003/0055397 A1 | 3/2003 | Zucker |
| 2003/0055454 A1 | 3/2003 | Zucker |
| 2003/0093116 A1 | 5/2003 | Nowakowski |
| 2003/0109869 A1 | 6/2003 | Shadduck |
| 2003/0120256 A1 | 6/2003 | Lary et al. |
| 2003/0125766 A1 | 7/2003 | Ding |
| 2003/0153060 A1 | 8/2003 | Wilson et al. |
| 2003/0191479 A1 | 10/2003 | Thornton |
| 2003/0195498 A1 | 10/2003 | Treat et al. |
| 2003/0199863 A1 | 10/2003 | Swanson et al. |
| 2003/0236518 A1 | 12/2003 | Marchitto et al. |
| 2004/0006333 A1 | 1/2004 | Arnold et al. |
| 2004/0010298 A1 | 1/2004 | Altshuler et al. |
| 2004/0030348 A1 | 2/2004 | Peterson et al. |
| 2004/0068306 A1 | 4/2004 | Shadduck |
| 2004/0092913 A1 | 5/2004 | Hennings et al. |
| 2004/0102797 A1 | 5/2004 | Golden et al. |
| 2004/0153054 A1 | 8/2004 | Lindenbaum et al. |
| 2004/0153060 A1 | 8/2004 | Lindenbaum et al. |
| 2004/0158287 A1 | 8/2004 | Cragg et al. |
| 2004/0199155 A1 | 10/2004 | Mollenauer |
| 2004/0199226 A1 | 10/2004 | Shadduck |
| 2004/0215232 A1 | 10/2004 | Belhe et al. |
| 2004/0220562 A1 | 11/2004 | Garabedian et al. |
| 2004/0249324 A1 | 12/2004 | Louis |
| 2004/0249342 A1 | 12/2004 | Khosravi et al. |
| 2004/0267307 A1 | 12/2004 | Bagaoisan et al. |
| 2005/0038419 A9 | 2/2005 | Arnold et al. |
| 2005/0085854 A1 | 4/2005 | Ginn |
| 2005/0192654 A1 | 9/2005 | Chanduszko et al. |
| 2005/0209637 A1 | 9/2005 | Zhu et al. |
| 2005/0228443 A1 | 10/2005 | Yassinzadeh |
| 2005/0267522 A1 | 12/2005 | Yassinzadeh et al. |
| 2005/0273095 A1 | 12/2005 | Taimisto et al. |
| 2005/0277980 A1 | 12/2005 | Yassinzadeh |
| 2006/0089637 A1 | 4/2006 | Werneth et al. |
| 2006/0190066 A1 | 8/2006 | Worthen |
| 2006/0206121 A1 | 9/2006 | Chin et al. |
| 2006/0235376 A1 | 10/2006 | Lindenbaum et al. |
| 2006/0253072 A1 | 11/2006 | Pai et al. |
| 2006/0271032 A1 | 11/2006 | Chin et al. |
| 2006/0276836 A1 | 12/2006 | Bergin et al. |
| 2007/0010391 A1 | 1/2007 | Mikijelj et al. |
| 2007/0021746 A1 | 1/2007 | Taimisto et al. |
| 2007/0021770 A1 | 1/2007 | Brenneman et al. |
| 2007/0049968 A1 | 3/2007 | Sibbitt et al. |
| 2007/0055223 A1 | 3/2007 | Eckhouse et al. |
| 2007/0100232 A1 | 5/2007 | Hiller et al. |
| 2007/0198057 A1 | 8/2007 | Gelbart et al. |
| 2007/0208330 A1 * | 9/2007 | Treat et al. ............ 606/30 |
| 2007/0213710 A1 | 9/2007 | Lindenbaum et al. |
| 2007/0233185 A1 | 10/2007 | Anderson et al. |
| 2007/0282975 A1 | 12/2007 | Kato |
| 2008/0009747 A1 | 1/2008 | Saadat et al. |
| 2008/0015569 A1 | 1/2008 | Saadat et al. |
| 2008/0039793 A1 | 2/2008 | Goldman et al. |
| 2008/0039829 A1 | 2/2008 | Goldman et al. |
| 2008/0065150 A1 | 3/2008 | Drasler et al. |
| 2008/0082122 A1 | 4/2008 | Khosravi et al. |
| 2008/0091193 A1 | 4/2008 | Kauphusman et al. |
| 2008/0154303 A1 | 6/2008 | Yassinzadeh |
| 2008/0167643 A1 | 7/2008 | Mizrahi et al. |
| 2008/0177300 A1 | 7/2008 | Mas et al. |
| 2009/0125056 A1 | 5/2009 | Buchbinder et al. |
| 2009/0149847 A1 | 6/2009 | Yadin et al. |
| 2009/0163903 A1 | 6/2009 | Lindenbaum et al. |
| 2010/0228241 A1 * | 9/2010 | Eckhouse et al. ............ 606/29 |

FOREIGN PATENT DOCUMENTS

| | | |
|---|---|---|
| CA | 2514865 A1 | 8/2004 |
| CA | 2587228 A1 | 5/2006 |
| DE | 3838840 A1 | 5/1990 |
| DK | 109688 A | 3/1988 |
| EP | 0075860 A2 | 4/1983 |
| EP | 0476178 A1 | 3/1992 |
| EP | 0482350 A2 | 4/1992 |
| EP | 0521595 A2 | 1/1993 |
| EP | 1096884 B1 | 5/2001 |
| EP | 1368089 A1 | 12/2003 |
| EP | 1599239 A2 | 11/2005 |
| EP | 1711117 B1 | 10/2006 |
| GB | 1 511 557 A | 5/1978 |
| GB | 2 054 385 A | 2/1981 |
| GB | 2060397 | 5/1981 |
| JP | 3-080847 A | 4/1991 |
| JP | 5-337131 A | 12/1993 |
| JP | 6-233779 A | 8/1994 |
| JP | 8-501947 A | 3/1996 |
| JP | 2001-190561 A | 7/2001 |
| JP | 2002-301088 A | 10/2002 |
| JP | 2003-067676 A | 3/2003 |
| JP | 2003220074 | 8/2003 |
| JP | 2006-516445 A | 7/2006 |
| JP | 2007-520306 A | 7/2007 |
| KR | 100944676 B1 | 3/2010 |
| WO | WO-90/14796 A1 | 12/1990 |
| WO | WO-92/05740 A1 | 4/1992 |
| WO | WO-92/22252 A1 | 12/1992 |
| WO | WO-93/21844 A1 | 11/1993 |
| WO | WO-94/01158 A1 | 1/1994 |

| | | |
|---|---|---|
| WO | WO-94/01199 A2 | 1/1994 |
| WO | WO-94/24948 A1 | 11/1994 |
| WO | WO-9632882 A1 | 10/1996 |
| WO | WO-97/09934 A1 | 3/1997 |
| WO | WO-98/11830 A1 | 3/1998 |
| WO | WO-9913779 A2 | 3/1999 |
| WO | WO-00/02488 A1 | 1/2000 |
| WO | WO-02/072188 | 9/2002 |
| WO | WO-2004/069300 A2 | 8/2004 |
| WO | WO-2004/069400 A1 | 8/2004 |
| WO | WO-2004/071612 A2 | 8/2004 |
| WO | WO-2005/074364 A2 | 8/2005 |
| WO | WO-2006/054170 A1 | 5/2006 |
| WO | WO-2007010391 | 1/2007 |
| WO | WO-2009/023866 A1 | 2/2009 |
| WO | WO-2009/046356 A1 | 4/2009 |

OTHER PUBLICATIONS

U.S. Appl. No. 60/935,484, filed Aug. 15, 2007, Mizrahi et al.
U.S. Appl. No. 60/960,604, filed Oct. 5, 2007, Mizrahi et al.
U.S. Appl. No. 61/006,926, filed Feb. 6, 2008, Mizrahi et al.
U.S. Appl. No. 09/598,232, filed Jun. 21, 2000, Mizrahi et al.
"About AVD", http://www.compressar.com/about/index.shtml; Advanced Vascular Dynamics; last accessed Jun. 22, 2009; (Copyright (2006)); (p. 1).
"Overview of CompressorAR®," http://www.compressar.com/products/index.shtml; Advanced Vascular Dynamics; (Copyright (2002)); (p. 1).
Abbott Vascular Devices—ProStar XL 10 www.perclose.com/products/product.php?id=19; last accessed Dec. 5, 2005; (Copyright 1996, 2004); (p. 1).
Sigel et al., "The Mechanism of Blood Vessel Closure by High Frequency Electrocoagulation," *Surgery Gynecology & Obstetrics*; (Oct. 1965); vol. 121, No. 4; (pp. 823-831).
K.K. Jain, et al., "Repair of small blood vessels with the Neodymium-YAG laser: A preliminary report", *Surgery*, vol. 85, No. 6; (1979) (pp. 684-688).
S. Silber, et al., "Vascular Closure Devices for Immediate Sheath Removal after Coronary Interventions: Luxury or Necessity?", *Handbook of Coronary Stents*, 3. ed.; (2000); pp. 147-151.
International Search Report in co-pending application No. PCT/IL04/00100; Dated: Oct. 15, 2004.
Angio-Seal™, 111, 2002, STS Platform Design.
European Search Report in co-pending application No. 02703826.4; Dated: Feb. 6, 2009.
European Search Report in co-pending application No. 99929684.1; Dated: Apr. 6, 2004.
International Search Report in co-pending application No. PCT/IL05/00122, issued Dec. 30, 2005.
International Search Report in co-pending application No. PCT/IB05/03491, issued Feb. 27, 2006.
International Search Report in co-pending application No. PCT/IL02/00200, issued Jul. 31, 2002.
International Search Report in co-pending application No. PCT/IL97/00309, issued Feb. 3, 1998.
International Search Report in co-pending application No. PCT/IL99/00384, issued Nov. 9, 1999.
International Search Report in co-pending application No. PCT/US08/73402, issued Oct. 22, 2008.
International Search Report in co-pending application No. PCT/US08/78826, issued Dec. 29, 2008.
European Search Report in co-pending application No. EP 08798045.4 issued Jul. 27, 2011.
Japanese Office Action in co-pending application No. JP 2007-542157 issued Feb. 1, 2012.
Canadian Office Action in co-pending application No. CA 2,514,865 issued Feb. 7, 2012.
European Office Action in co-pending application No. EP 05 703 165.0 issued Mar. 29, 2010.
European Office Action in co-pending application No. EP 05 703 165.0 issued Dec. 21, 2009.
European Office Action in co-pending application No. EP 04 707 612.0 issued Sep. 7, 2011.
Korean Notice of Grounds for Refusal in co-pending application No. 10-2003-7012034 issued Dec. 14, 2007.
Korean Notice of Grounds for Refusal in co-pending application No. 10-2003-7012034 issued Jun. 16, 2008.
Korean Notice of Grounds for Refusal in co-pending application No. 10-2003-7012034 issued Feb. 24, 2009.
In the U.S. Patent and Trademark Office, Non-Final Office Action in re: U.S. Appl. No. 11/791,448, dated Feb. 7, 2012, 12 pages.
In the U.S. Patent and Trademark Office, Non-Final Office Action in re: U.S. Appl. No. 10/543,654, dated Aug. 26, 2009, 11 pages.
In the U.S. Patent and Trademark Office, Final Office Action in re: U.S. Appl. No. 10/543,654, dated Jul. 7, 2010, 10 pages.
In the U.S. Patent and Trademark Office, Examiners Interview Summary in re: U.S. Appl. No. 10/543,654, dated Aug. 10, 2010, 3 pages.
In the U.S. Patent and Trademark Office, Restriction Requirement in re: U.S. Appl. No. 10/543,654, dated Jan. 22, 2009, 6 pages.
In the U.S. Patent and Trademark Office, Non-Final Office Action in re: U.S. Appl. No. 10/543,654, dated Oct. 26, 2009, 12 pages.
In the U.S. Patent and Trademark Office, Final Office Action in re: U.S. Appl. No. 10/543,654, dated Jul. 7, 2010, 11 pages.
In the U.S. Patent and Trademark Office, Examiner Interview Summary in re: U.S. Appl. No. 09/114,817, dated Oct. 20, 1999, 1 page.
In the U.S. Patent and Trademark Office, Non-Final Office Action in re: U.S. Appl. No. 09/114,817, dated Aug. 24, 1999, 5 pages.
In the U.S. Patent and Trademark Office, Examiner;s Interview Summary in re: U.S. Appl. No. 10/288,843, dated Mar. 1, 2005, 1 page.
In the U.S. Patent and Trademark Office, Non-Final Office Action in re: U.S. Appl. No. 10/288,843, dated Jan. 11, 2005, 4 pages.
In the U.S. Patent and Trademark Office, Notice of Allowance in re: U.S. Appl. No. 09/808,630, dated Oct. 6, 2003, 9 pages.
In the U.S. Patent and Trademark Office, Non-Final Office Action in re: U.S. Appl. No. 09/808,630, dated Sep. 17, 2003, 1 page.
In the U.S. Patent and Trademark Office, Non-Final Office Action in re: U.S. Appl. No. 09/808,630, dated Nov. 25, 2002, 5 pages.
In the U.S. Patent and Trademark Office, Final Office Action in re: U.S. Appl. No. 11/797,294, dated Jul. 26, 2011, 17 pages.
In the U.S. Patent and Trademark Office, Examiners Interview Summary in re: U.S. Appl. No. 11/797,294, dated Jun. 17, 2010, 4 pages.
In the U.S. Patent and Trademark Office, Notice of Allowance in re: U.S. Appl. No. 09/114,817 dated Dec. 16, 1999, 5 pages.
In the U.S. Patent and Trademark Office, Restriction Requirement in re: U.S. Appl. No. 09/598,232, dated Jun. 5, 2002, 4 pages.
In the U.S. Patent and Trademark Office, Non-Final Office Action in re: U.S. Appl. No. 09/598,232, dated Jul. 16, 2002, 7 pages.
In the U.S. Patent and Trademark Office, Notice of Allowance in re: U.S. Appl. No. 10/288,843, dated Jul. 6, 2005, 6 pages.
In the U.S. Patent and Trademark Office, Non-Final Office Action in re: U.S. Appl. No. 09/808,630, dated Aug. 18, 2003, 5 pages.
In the U.S. Patent and Trademark Office, Restriction Requirement in re: U.S. Appl. No. 09/808,630, dated Jun. 26, 2002, 4 pages.
In the U.S. Patent and Trademark Office, Non-Final Office Action in re: U.S. Appl. No. 11/791,277 dated Apr. 20, 2011, 9 pages.
In the U.S. Patent and Trademark Office, Final Office Action in re: U.S. Appl. No. 11/791,277 dated Dec. 6, 2011, 12 pages.
In the U.S. Patent and Trademark Office, Final Office Action in re: U.S. Appl. No. 08/715,160, dated Jul. 9, 1997, 7 pages.
In the U.S. Patent and Trademark Office, Non-Final Office Action in re: U.S. Appl. No. 08/715,160, dated Feb. 26, 1997, 6 pages.
In the U.S. Patent and Trademark Office, Notice of Allowance in re: U.S. Appl. No. 08/715,160, dated Oct. 2, 1997, 7 pages.
In the U.S. Patent and Trademark Office, Examiners Interview Summary in re: U.S. Appl. No. 08/715,160, dated Sep. 29, 1997, 6 pages.
In the U.S. Patent and Trademark Office, Non- Final Office Action in re: U.S. Appl. No. 11/471,537, dated Sep. 4, 2008, 6 pages.
In the U.S. Patent and Trademark Office, Non-Final Office Action in re: U.S. Appl. No. 11/797,294, dated Nov. 13, 2008, 12 pages.
In the U.S. Patent and Trademark Office, Final Office Action in re: U.S. Appl. No. 11/797,294, dated Jul. 7, 2009, 12 pages.
In the U.S. Patent and Trademark Office, Non-Final Office Action in re: U.S. Appl. No. 11/797,294, dated Jan. 15, 2010, 12 pages.
In the U.S. Patent and Trademark Office, Final Office Action in re: U.S. Appl. No. 11/797,294, dated Aug. 24, 2010, 12 pages.
In the U.S. Patent and Trademark Office, Non-Final Office Action in re: U.S. Appl. No. 11/797,294, dated Feb. 25, 2011, 2010, 16 pages.

In the U.S. Patent and Trademark Office, Non-Final Office Action in re: U.S. Appl. No. 13/302,6621 dated Mar. 12, 2012, 15 pages.
In the U.S. Patent and Trademark Office, Examiners Interview Summary in re: U.S. Appl. No. 10/358,130, dated Dec. 7, 2005, 1 page.
In the U.S. Patent and Trademark Office, Non-Final Office Action in re: U.S. Appl. No. 10/616,887, dated Aug. 24, 2005, 7 pages.
In the U.S. Patent and Trademark Office, Final Office Action in re: U.S. Appl. No. 10/616,887, dated May 22, 2006, 7 pages.
In the U.S. Patent and Trademark Office, Notice of Allowance in re: U.S. Appl. No. 10/616,887, dated Jan. 24, 2007, 8 pages.
In the U.S. Patent and Trademark Office, Examiners Interview Summary in re: U.S. Appl. No. 10/616,887, dated Jun. 26, 2006, 3 pages.
In the U.S. Patent and Trademark Office, Examiners Interview Summary in re: U.S. Appl. No. 10/616,887, dated Mar. 1, 2006, 3 pages.
In the U.S. Patent and Trademark Office, Restriction Requirement in re: U.S. Appl. No. 10/616,887, dated May 31, 2005, 5 pages.
In the U.S. Patent and Trademark Office, Restriction Requirement in re: U.S. Appl. No. 12/245,569, dated Apr. 14, 2011, 9 pages.
In the U.S. Patent and Trademark Office, Non-Final Office Action in re: U.S. Appl. No. 12/245,569, dated Jul. 14, 2011, 9 pages.
In the U.S. Patent and Trademark Office, Final Office Action in re: U.S. Appl. No. 12/245,569, dated Nov. 30, 2011, 8 pages.
Europeam Search Report in co-pending application No. EP 08836162 issued May 10, 2012.

* cited by examiner

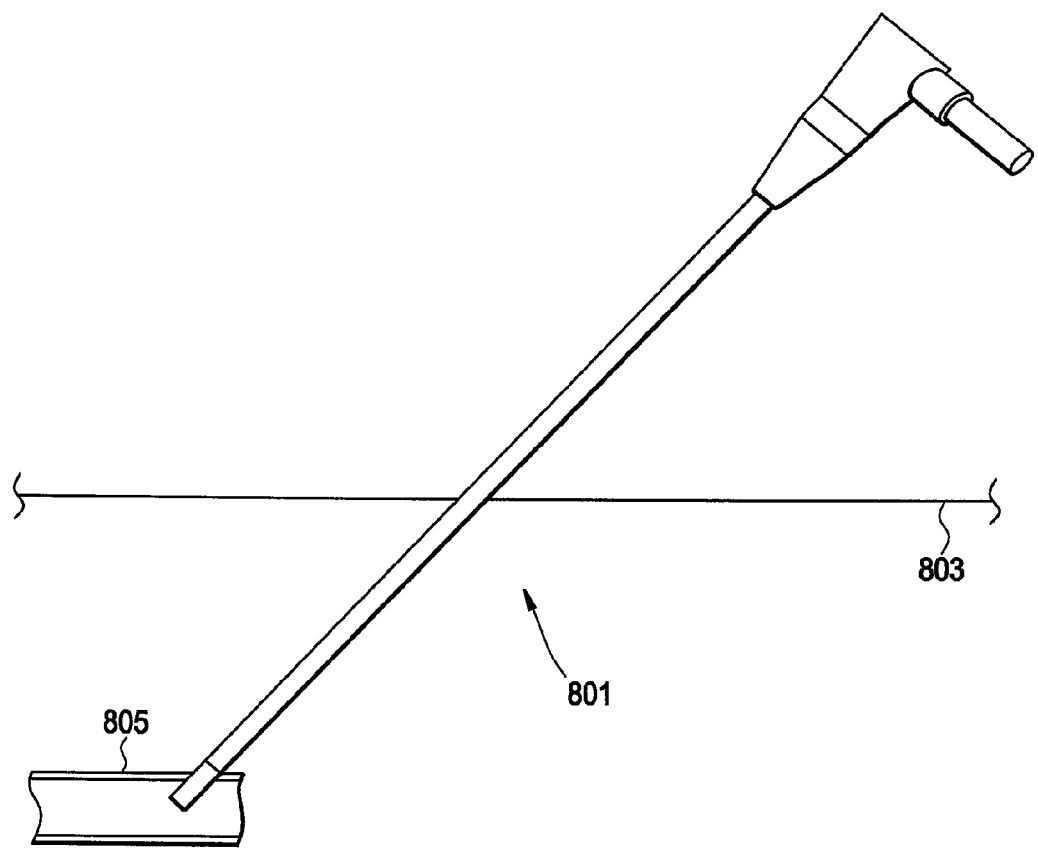

SYSTEMS AND METHODS FOR PUNCTURE CLOSURE

CROSS-REFERENCE TO RELATED APPLICATIONS

This application claims priority to U.S. Provisional Patent Application No. 60/935,484, filed Aug. 15, 2007, U.S. Provisional Patent Application No. 60/960,604, filed Oct. 5, 2007, and U.S. Provisional Patent Application No. 61/006,926, filed Feb. 6, 2008, the contents of which are incorporated by reference herein in their entireties.

FIELD OF THE INVENTION

The invention relates generally to methods and apparatus for treating vasculatures, and, more particularly, to methods and apparatus for post-catheterization closure of punctures in vessel walls.

BACKGROUND OF THE INVENTION

Various therapeutic and diagnostic procedures, such as arterial catheterization, cause punctures to the vasculature of a patient. Following the performance of such procedures, it is necessary to promote hemostasis quickly and without undue hardship for the patient. Current systems may be either inefficient or painful for a patient.

Generally, needs exist for improved apparatuses and methods for treating vasculatures. More specifically, needs exist for improved apparatuses and methods for efficiently and effectively closing a puncture in a vasculature.

SUMMARY OF THE INVENTION

Embodiments of the present invention solve many of the problems and/or overcome many of the drawbacks and disadvantages of the prior art by providing apparatuses and method for closing punctures in a wall of a vasculature.

In particular, embodiments of the invention may include an apparatus for closing a puncture in a vessel wall including an anchor shaft, an anchor coupled to a distal end of the anchor shaft wherein the anchor is deployed within a vessel lumen and moved into contact with an inner surface of a vessel wall, a heating element for passing over the anchor shaft to a position a predetermined distance from the anchor, wherein the heating element is not within the vessel lumen, and wherein tissue is compressed between the anchor and the heating element during activation of the heating element.

The anchor may be selected from the group consisting of a balloon, a T-anchor, an expansible cage, a floating anchor, and combinations thereof. A positioning device may pass over the anchor shaft. The positioning device may be selected from the group consisting of a balloon, a sponge, an expansible cage, and combinations thereof. The heating element may be selected from the group consisting of flat-ended, dome-shaped, flattened dome-shaped, and combinations thereof. The heating element may include a patterned conducting element. A coating may be on the heating element. The coating on the heating element may be silicone. The heating element may include two or more segments coupled together to create a unified heating element. The heating element may be flexible. The heating element may be positioned by movement of a shaft of an introducer, wherein the shaft retains the heating element in a compressed position until withdrawal of the introducer shaft. The heating element may be positioned by expansion of a positioning device. The heating element may be rigid. The predetermined distance may be approximately 1-2 mm.

Embodiments may also include a method of closing a puncture in a vessel wall including providing an apparatus having an anchor shaft, an anchor coupled to a distal end of the anchor shaft, and a heating element, inserting the distal end of the anchor shaft into a vessel lumen through a puncture, deploying the anchor within the vessel lumen, inserting the heating element to a position a predetermined distance from the anchor, wherein the heating element is not within the vessel lumen and tissue is compressed between the anchor and the heating element, withdrawing the anchor device through the heating element, activating the heating element, and withdrawing the heating element.

The anchor may be moved against an inner surface of the vessel wall proximate to the puncture prior to inserting the heating element. The anchor may be selected from the group consisting of a balloon, a T-anchor, an expansible cage, a floating anchor, and combinations thereof. A positioning device may be inserted over the anchor shaft. The positioning device may be selected from the group consisting of a balloon, a sponge, an expansible cage, and combinations thereof. The heating element may be selected from the group consisting of a flat-ended heating element, a dome-shaped heating element, a flattened dome-shaped heating element, and combinations thereof. The heating element may have one or more segments coupled together to create a unified heating element. The heating element may be flexible.

Embodiments of the present invention may include an apparatus for closing a puncture in a vessel wall including an anchor shaft, an anchor coupled to a distal end of the anchor shaft wherein the anchor is deployed within a vessel lumen and moved into contact with an inner surface of a vessel wall, and a two-stage heating element passing over the anchor shaft into proximity with an outer surface of the vessel wall opposite the anchor.

The anchor may be selected from the group consisting of a balloon, a T-anchor, an expansible cage, a floating anchor, and combinations thereof. The heating element may be selected from the group consisting of a flat-ended heating element, a dome-shaped heating element, a flattened dome-shaped heating element, and combinations thereof. The first stage of the two-stage heating element may apply heat sufficient to minimally bind the vessel wall to the heating element. The second stage of the two-stage heating element may apply heat sufficient to close the vessel wall. The anchor device may be withdrawn through the heating element prior to the second stage. The vessel wall and tissue may be sandwiched between the anchor and the heating element. The heating element may be controlled by a handheld unit.

Embodiments may also include a method of closing a puncture in a vessel wall including providing an apparatus having an anchor shaft, an anchor coupled to a distal end of the anchor shaft, and a heating element, inserting the distal end of the anchor shaft into a vessel lumen through a puncture, deploying the anchor within the vessel lumen, inserting the heating element into the vicinity of the puncture, initially heating the heating element for minimally adhering tissue to the heating element, withdrawing the anchor device through the heating element, completely activating the heating element, and withdrawing the heating element.

Tissue may be sandwiched between the anchor and the heating element. The anchor may be selected from the group consisting of a balloon, a T-anchor, an expansible cage, a floating anchor, and combinations thereof. The heating element may be selected from the group consisting of a flat-ended heating element, a dome-shaped heating element, a flattened dome-shaped heating element, and combinations thereof.

Embodiments of the present invention may include an apparatus for closing a puncture in a vessel wall including an anchor shaft, an anchor coupled to a distal end of the anchor shaft wherein the anchor is deployed within a vessel lumen and moved into contact with an inner surface of a vessel wall, a heating element adapted to pass over the anchor shaft into proximity with an outer surface of the vessel wall opposite the anchor, and a pass-through device at least partially surrounding the anchor shaft for facilitating passage of the heating element over the anchor shaft into proximity with the outer surface of the vessel wall opposite the anchor.

The anchor may be selected from the group consisting of a balloon, a T-anchor, an expansible cage, a floating anchor, and combinations thereof. The anchor may be a nitinol cage covered by a membrane. The membrane may include at least silicone. The nitinol cage may be substantially planar in an expanded position. The heating element may be selected from the group consisting of a flat-ended heating element, a dome-shaped heating element, a flattened dome-shaped heating element, and combinations thereof. The heating element may be a two-stage heating element. The first stage of the two-stage heating element may apply heat sufficient to minimally bind the vessel wall to the heating element. The second stage of the two-stage heating element may apply heat sufficient to substantially close the vessel wall. The anchor device may be withdrawn through the heating element prior to the second stage. The vessel wall and tissue may be sandwiched between the anchor and the heating element. A guide wire may be deployed within a vessel lumen with the anchor shaft, wherein the guide wire remains within the vessel lumen after removal of the anchor. The guide wire may indicate position of the heating element relative to the vessel wall. The pass-through device may be a roll coupled to the anchor shaft. The roll may have one or more slits for allowing expansion of the roll. The pass-through device may be a dilator. Indicator marks may be located on an anchor shaft coupled to the anchor, wherein the indicators indicate a correct position of the anchor. A large tip may be located on the anchor, wherein the large tip fits flush with a distal end of the heating element when the anchor is withdrawn.

Embodiments may also include a method of closing a puncture in a vessel wall including providing an apparatus having an anchor shaft, an anchor coupled to a distal end of the anchor shaft, a pass-through device at least partially surrounding the anchor shaft, and a heating element, inserting the distal end of the anchor shaft into a vessel lumen through a puncture, deploying the anchor within the vessel lumen, inserting the heating element into the vicinity of the puncture by passing the heating element through the pass-through device, withdrawing the pass-through device after positioning the heating element, activating the heating element, withdrawing the anchor, and withdrawing the heating element.

The pass-through device may be withdrawn by applying pressure away from a distal end of the anchor shaft. Activating the heating element may include initially heating the heating element for minimally adhering tissue to the heating element, and secondarily heating the heating element. The anchor may be withdrawn through the heating element between the initial heating and the secondary heating. Tissue may be sandwiched between the anchor and the heating element. The anchor may be selected from the group consisting of a balloon, a T-anchor, an expansible cage, a floating anchor, and combinations thereof. The heating element may be selected from the group consisting of a flat-ended heating element, a dome-shaped heating element, a flattened dome-shaped heating element, and combinations thereof. A guide wire may be inserted into the vessel lumen with the anchor. Position of the heating element may be measured with the guide wire.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE PREFERRED EMBODIMENTS

Embodiments of the present invention may include apparatus and methods for closing a puncture in a vessel wall. An apparatus of the present invention may have various combinations of an anchoring device, a positioning device and/or a heating element for closing a puncture within a vessel wall. An anchoring device may be a balloon, an expansible cage and/or a wire operated T-anchor. A positioning device may be a balloon, a sponge, and/or an expansible cage. A heating element may be flexible or rigid and preferably provides heat to target tissue through conduction. The heating element may be directly in contact with a vessel wall or may be placed in the vicinity of a vessel wall. These various elements may be used in various combinations as desired and/or depending on a particular application.

Anchoring systems may be used to provide stability during a puncture closure procedure. An anchoring system may act as a locating system for positioning a heating element over a puncture site. Anchoring systems of the present invention may generally be inserted into a vessel through an introducer shaft. The anchoring systems may then be deployed with a vessel lumen and moved into contact with an inner surface of a vessel wall adjacent the puncture site. The anchoring systems described below may be used interchangeably with the various embodiments of the present invention depending on a particular application.

Figure 1:
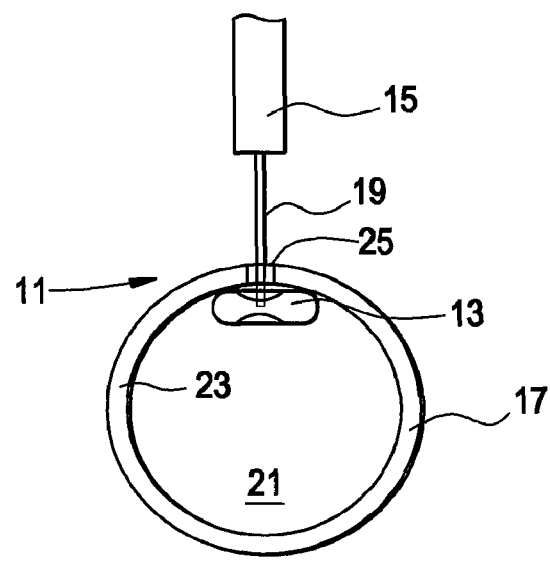
FIG. 1 illustrates an embodiment of a balloon anchoring system.

FIG. 1 illustrates a balloon anchoring system 11. Balloon anchoring systems 11 are generally illustrated throughout the description of the embodiments of the present invention, but it is understood that the types of anchoring systems are interchangeable. An anchor balloon 13 may be inserted through an introducer shaft 15. The introducer shaft 15 may initially be inserted through a vessel wall 17 and into a vessel lumen 21 during a procedure. The introducer shaft preferably has a diameter of about 5-7 French ("Fr"). The introducer shaft may have an inner diameter of approximately 1.6 mm-2.3 mm and may have an outer diameter of approximately 1.7-2.5 mm. The anchor balloon 13 may be located on a distal end of an anchor shaft 19. A proximal end of the anchor shaft 19 may be in fluid communication with a source of fluid for inflating and deflating the anchor balloon 13. When a distal end of the anchor shaft 19 is within the vessel lumen 21, the anchor balloon 13 is inflated to a desired volume. The introducer shaft 15 may be left in place after a procedure creating a puncture in a vessel wall and during insertion of the anchor balloon 13, but may be withdrawn partially, as shown in FIG. 1, or completely after inflation of the anchor balloon 13. FIG. 1 shows the introducer shaft 15 withdrawn from the vessel lumen 21 and the anchor balloon 13 moved into contact with an inner surface 23 of the vessel wall 17 near a puncture 25. When in an inflated state, the anchor balloon 13 preferably prevents blood from passing through a puncture 25 in the vessel wall 17 because the anchor balloon 13 preferably has a larger diameter than the puncture 25 when the anchor balloon 13 is in an expanded state. The anchor balloon 13 may be removed from the vessel lumen 21 by deflating the anchor balloon 13. The anchor balloon 13 may have various configurations in accordance with the principles of the invention depending on a particular application, use or indication.

Figure 2:
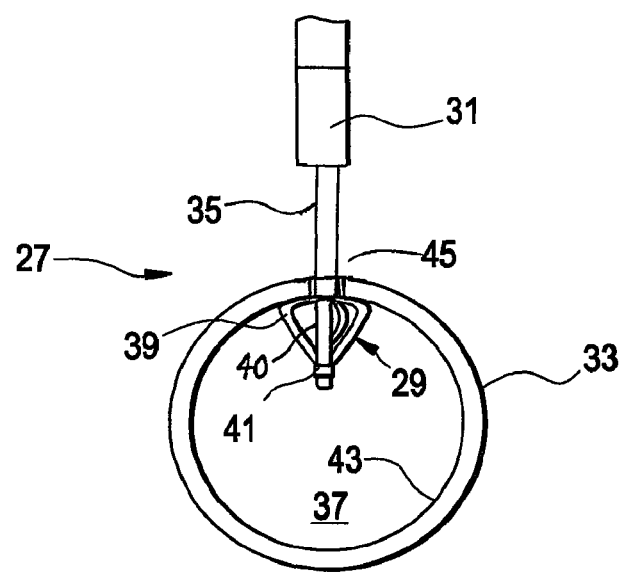
FIG. 2 illustrates an embodiment of an expansible cage anchoring system.

FIG. 2 illustrates an expansible cage anchoring system 27. An expansible anchor cage 29 may be formed from various materials depending on a particular application, but are preferably made from nitinol or shape-memory materials. The cage anchoring system 27 may have various configurations depending on particular uses. The expansible anchor cage 29 may be inserted through an introducer shaft 31. An introducer shaft 31 may first be inserted through a vessel wall 33 during a procedure. A proximal end of the expansible anchor cage 29 may be coupled to a distal end of an anchor shaft 35. A distal end of the expansible anchor cage 29 may be coupled to a distal end of an interior shaft 40. The interior shaft 40 may be operated to move coaxially with the anchor shaft 35. The expansible anchor cage 29 may automatically expand upon exiting the introducer shaft 31. Alternatively, the expansible anchor cage 29 may be expanded via a force from the anchor shaft 35. For example, the expansible anchor cage 29 may be in a compressed position when inserted into a vessel lumen 37. The anchor shaft 35 may then be operated to position arms 39 on the anchor cage 29 into an expanded position either by self-expansion or by moving the anchor shaft 35 distally towards a tip 41 of an interior shaft 40. The relative movement of the anchor shaft 35 and the interior shaft 40 may force the arms 39 to move outward. The anchor shaft 35 may move distally over the interior shaft 40 towards the tip 41 and/or the interior shaft 40 may move proximally through the anchor shaft 35 such that the tip 41 moves towards the distal end of the anchor shaft 35. When a distal end 41 of the interior shaft 40 is within a vessel lumen 37, the anchor cage 29 may be deployed in an expanded state within the vessel lumen 37. FIG. 2 shows the introducer shaft 31 withdrawn from the vessel lumen 37 and the anchor cage 29 moved into contact with an inner surface 43 of the vessel wall 33. When in an expanded state, the expansible anchor cage 29 preferably prevents blood from passing through a puncture 45 in the vessel wall 33 because the anchor cage 29 preferably has a larger diameter than the puncture 45 when the anchor cage 29 is in an expanded state. The expansible anchor cage 29 may be collapsed for removal. The expansible anchor cage 29 may be removed from the vessel lumen 37 by moving the anchor shaft 35 coaxially over the interior shaft 40 away from the tip 41. This movement may force the arms 39 to compress to allow removal of the anchor cage 29 through the puncture 45. The expansible anchor cage 29 may have various configurations depending on a particular application.

Figure 3:
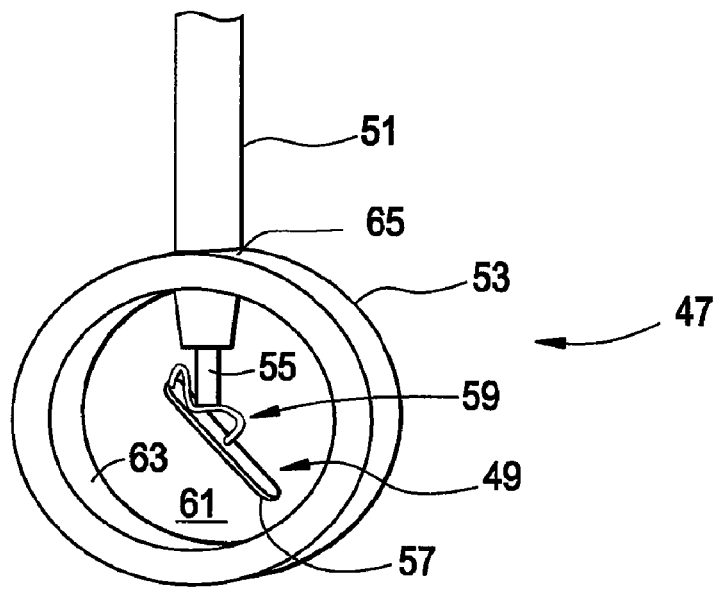
FIG. 3 illustrates an embodiment of a wire operated T-anchor system.

FIG. 3 illustrates a wire operated T-anchor system 47. The T-anchor system 47 may have various configurations depending on particular uses. A T-anchor 49 may be inserted through an introducer shaft 51. The introducer shaft 51 may first be inserted through a vessel wall 53 during a procedure and left in place until deployment of the T-anchor 49. The T-anchor 49 may be located on a distal end of an anchor shaft 55. The T-anchor 49 may be inserted through the introducer shaft 51 in a vertically oriented position with an anchor bar 57 inline with an anchor shaft 55. One or more operating wires 59 may be connected from the anchor bar 57 through the anchor shaft 55 to a proximal end of a catheter. The anchor bar 57 position may be altered by pulling an operating wire 59. Preferably, one operating wire pulls the anchor bar 57 into a horizontal position and another operating wire pulls the anchor bar 57 into a vertical position. Alternative arrangements and operations of operating wires 59 are possible depending on particular applications. The introducer shaft 51 may be withdrawn from a vessel lumen 61 and the T-anchor 49 moved into contact with an inner surface 63 of a vessel wall 53 into a substantially horizontal position, in other words, perpendicular to the T-anchor 49. When in a horizontal position, the T-anchor 49 preferably prevents blood from passing through a puncture 65 in the vessel wall 53 because the T-anchor 49 preferably has a larger diameter than the puncture 65. The T-anchor 49 may be removed from the vessel lumen 61 by operating the one or more operating wires to move the anchor bar 57 into a vertical position.

Positioning systems may be used to provide stability during a puncture closure procedure. Positioning systems may also act as a locating system for accurately positioning a heating element over a puncture site. Positioning systems of the present invention may generally be inserted into tissue surrounding a vessel through an introducer shaft. The positioning systems may then be deployed within the tissue. The positioning systems described below may be used interchangeably with the various embodiments of the present invention depending on a particular application.

Figure 4A:
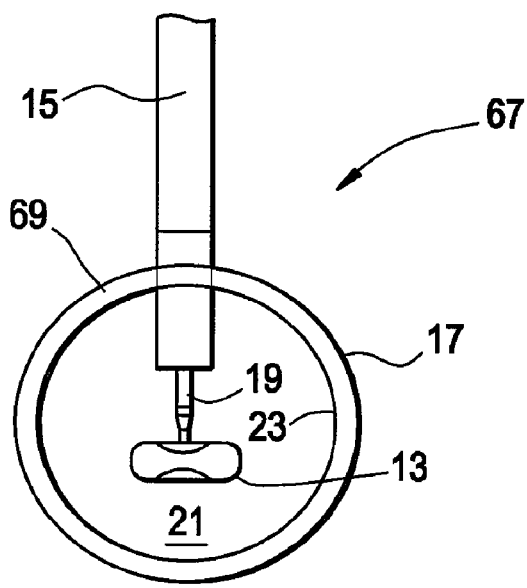
FIGS. 4A-4D illustrate an embodiment of a balloon positioning system.
Figure 4B:
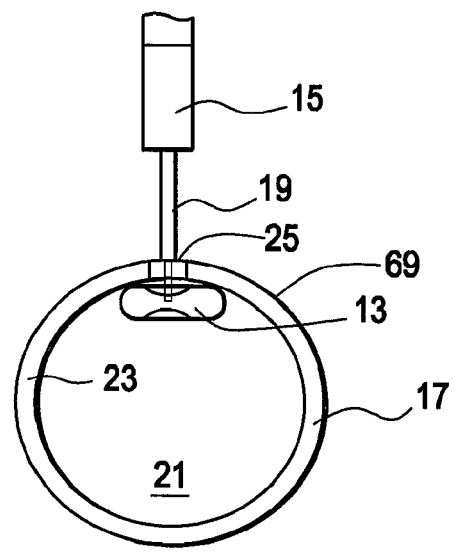
Figure 4C:
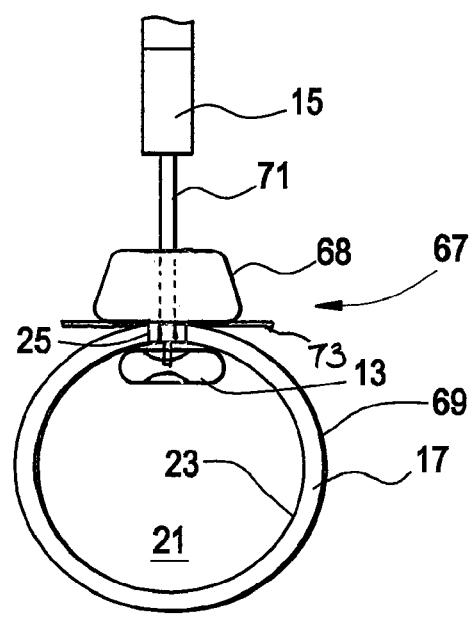
Figure 4D:
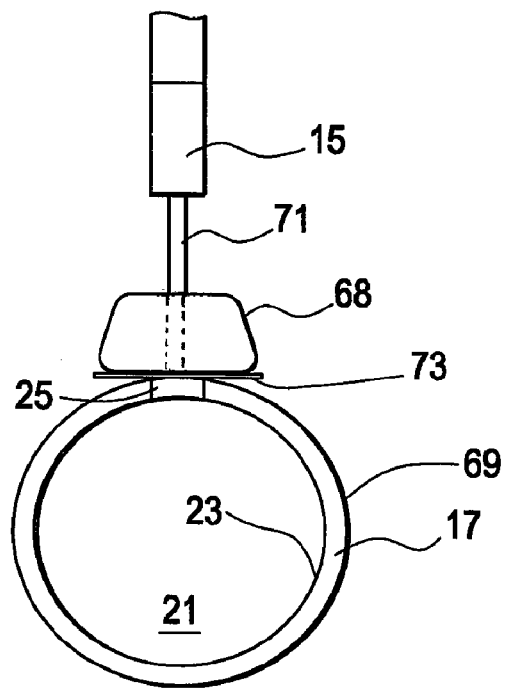

FIGS. 4A-4D illustrate a balloon positioning system 67 in combination with the balloon anchoring system 11 of FIG. 1. The balloon positioning system 67 may be used interchangeably with all types of anchoring systems, but is used with the system of FIG. 1 for illustration purposes. FIG. 4A shows the inflation of the anchor balloon 13 on a distal end of an anchor shaft 19. The anchor balloon 13 may be inflated within a vessel lumen 21. FIG. 4B shows removal of the introducer shaft 15 from the vessel lumen 21 and movement of the anchor balloon 13 into contact with an inner surface 23 of the vessel wall 17. FIG. 4C shows inserting a positioning balloon 68 on a positioning shaft 71 over the anchor shaft 19. The positioning balloon 68 may be inflated in a position near or in contact with an outer surface 69 of the vessel wall 17 and near or in contact with a puncture 25. The positioning balloon 68 may be inflated at various predetermined distances from the outer surface 69 of the vessel wall 17 depending on particular applications. The positioning balloon 68 may be inflated to a desired size and shape via the positioning shaft 71. The positioning shaft 71 may be in fluid communication with a source of fluid for inflating and deflating the positioning balloon 68. Various size and shape positioning balloons 68 may be used for various applications. A flexible heating element 73 may be deployed with the expansion of the positioning balloon 68. Once the positioning balloon 68 has been inflated and the heating element 73 deployed, the anchor balloon 13 may be deflated. The deflated anchor balloon 13 may then be withdrawn into and through the positioning shaft 71 for removal from the patient. The anchor balloon 13 has been removed as shown in FIG. 4D. The heating element 73 may then be activated to close the puncture 25. The positioning balloon 68 may then be deflated and the positioning balloon 68 along with the heating element 73 may be withdrawn into the introducer shaft 15 or may be otherwise removed from the patient.

Figure 5:
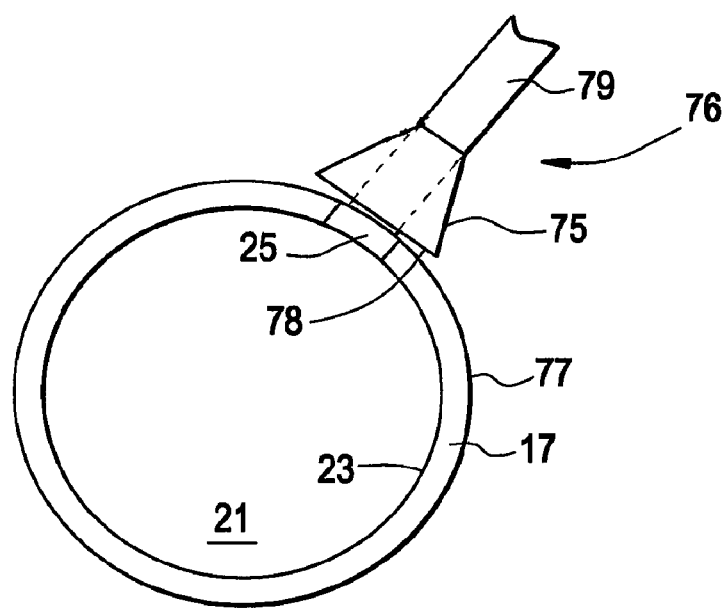
FIG. 5 illustrates an embodiment of a sponge positioning system.

FIG. 5 illustrates a sponge positioning system 76, which operates similarly to the positioning balloon 68 of FIGS. 4A-4D, in combination with the balloon anchoring system 11 of FIG. 1. The sponge positioning system 76 may be used interchangeably with all types of anchoring systems, but is used with the system of FIG. 1 for illustration purposes. The anchor balloon 13, as shown in FIG. 1, may be inflated within a vessel lumen 21. The introducer shaft 15, as shown in FIG. 1, may be removed from the vessel lumen 21 and the anchor balloon 13 on an anchor shaft 19, both shown in FIG. 1, may be moved into contact with an inner surface 23 of the vessel wall 17. The positioning sponge 75 may be inserted to a desired position along a positioning shaft 79. The positioning sponge 75 may be expanded in a position near or in contact with an outer surface 77 of the vessel wall 17 and near or in contact with the puncture 25. The positioning sponge 75 may be expanded at various distances from the outer surface 77 of the vessel wall 17 depending on particular applications. Various size and shape positioning sponges 75 may be used for various applications. Once the positioning sponge 75 has been expanded in a desired position, the anchor balloon 13, as shown in FIG. 1, may be deflated. The deflated anchor balloon 13 may then be withdrawn into the positioning shaft 79. A heating element 78, which may be adjacent and/or coupled to a base of the sponge 75, may then be activated to close the puncture 25. The positioning sponge 75 may then be compressed and withdrawn into and through the introducer shaft 15 or may be otherwise removed from the patient.

Figure 6:
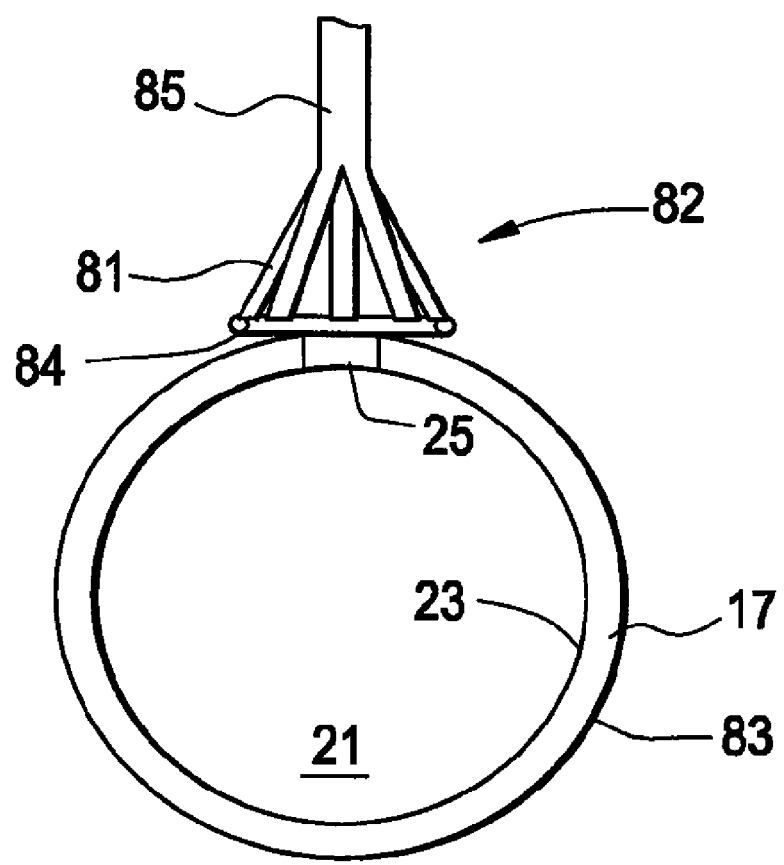
FIG. 6 illustrates an embodiment of an expansible cage positioning system.

FIG. 6 illustrates an expansible cage positioning system 82, which operates similarly to the positioning balloon 68 of FIGS. 4A-4D and the positioning sponge 75 of FIG. 5, in combination with the balloon anchoring system 11 of FIG. 1. The expansible cage positioning system 82 may be used interchangeably with all types of anchoring systems, but is used with the system of FIG. 1 for illustration purposes. An expansible positioning cage 81 may be made of nitinol or a shape-memory material as described above for the anchoring devices. The expansible positioning cage 81 may have various configurations depending on a particular application. The anchor balloon 13, as shown in FIG. 1, may be inflated within a vessel 21. An introducer shaft 15, as shown in FIG. 1, may be removed from the vessel lumen 21 and the anchor balloon 13 may be moved into contact with an inner surface 23 of the vessel wall 17. The expansible positioning cage 81 may be expanded in a position near and/or in contact with an outer surface 83 of the vessel wall 17 near and/or in contact with the puncture 25. The expansible cage may be expanded at various distances from the outer surface 83 of the vessel wall 17 depending on particular applications. The expansible cage 81 may be expanded to a desired size and shape via the introducer shaft 15. The expansible cage 81 may be contained by an introducer shaft prior to deployment. The expansible cage 81 may be deployed by removing the compression force associated with the introducer shaft 15 by withdrawing the introducer shaft 15. Various size and shape expansible cages 81 may be used for various applications. Once the expansible cage has been expanded in a desired location, the anchor balloon 13 may be deflated. The deflated anchor balloon 13 may then be withdrawn into the positioning shaft 85. A heating element 84 may then be activated to close the puncture 25. The expansible positioning cage 81 may then be recompressed by passing the introducer shaft 15 over at least part of the expansible cage 81. Movement of the introducer shaft 15 over at least part of the expansible cage 81 may cause compression of the expansible cage 81 into a compact configuration for removal from the patient.

Heating elements may be used to close a puncture within a vessel wall. Heating elements of the present invention are preferably conduction heating elements which may or may not directly contact target tissue. Heating elements may use resistor-type technology, INCONEL, or other heating element materials. Other types of heating elements, however, such as radio frequency, laser and others, may be used for particular applications. Heating elements may have various shapes for various applications. Flat-ended or flattened heating elements may be preferred for applications where the heating element is inserted perpendicular to a vessel wall. A flat-ended heating element may allow more heating surface to be brought into contact with a vessel wall. Dome-shaped heating elements may preferably be used in applications where the apparatuses of the present invention are inserted at various angles in comparison with a vessel wall. The term "dome-shaped" may be defined for purposes of the specification as any generally curved surface such as, but not limited to, spheres, partial spheres, flattened spheres, and/or circular or elliptical members. In some applications, a dome-shaped heating element may also be desirable in situations where an apparatus is inserted perpendicular to a vessel wall. Heating elements may be rigid or flexible depending on particular applications. Heating elements may have a non-stick coating, such as silicone, TEFLON, or other similar materials to prevent permanent adhering of the vessel walls and/or other tissue to the heating elements. Heating elements may be heated by passing current through a wire or other similar conducting element. Conducting elements may have various configurations to deliver customized heating patterns for particular applications. Various patterns of conducting elements may allow for various treatments.

Heating elements may be coupled to distal ends of heating element shafts. Heating element shafts may be adjacent to and slide coaxially with anchor shafts.

Figure 7:
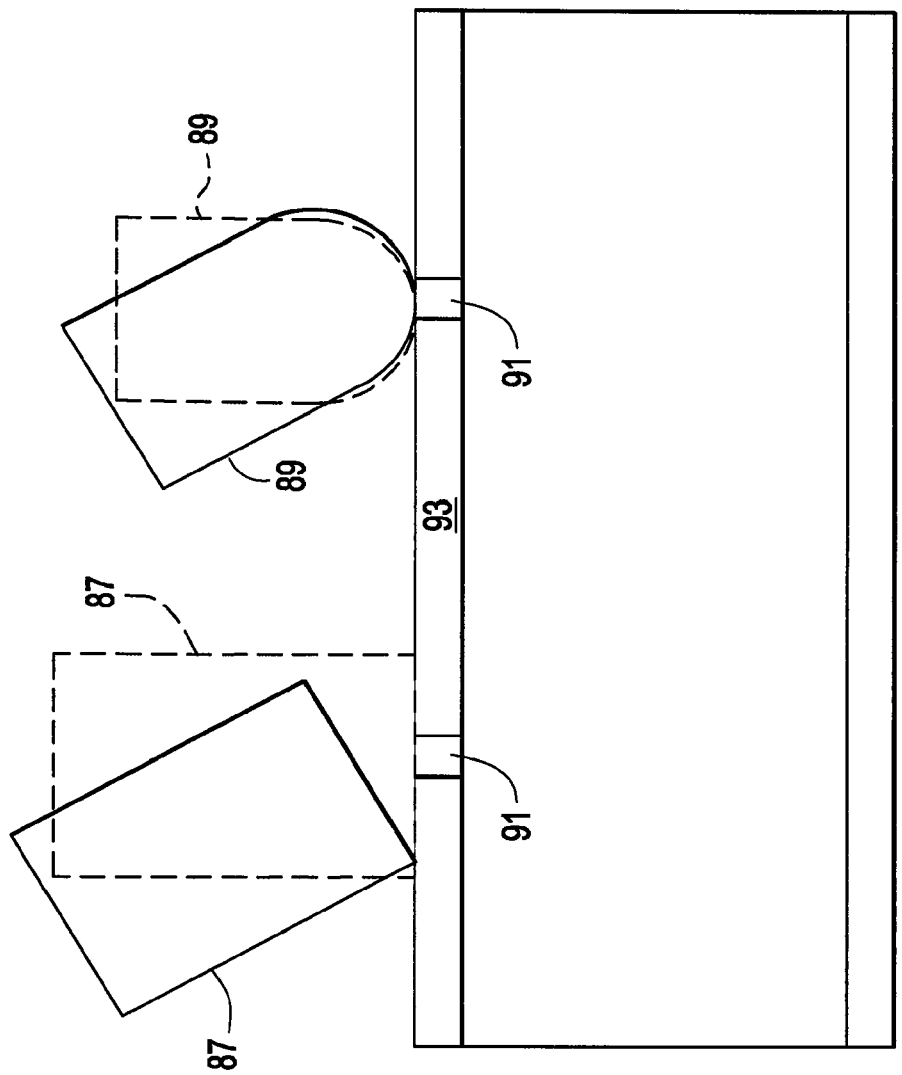
FIG. 7 illustrates an embodiment of a comparison between flat-ended and dome-shaped heating elements.

FIG. 7 shows a comparison between flat-ended heating element 87 and dome-shaped heating element 89 to arteriotomy punctures 91 through a vessel wall 93. FIG. 7 shows application of the heating elements at angles of 60 degrees (heating elements shown in solid lines) and 90 degrees (heating elements shown in dashed lines), respectively. Other angles are possible. Generally, when heating elements are applied at angles of other than 90 degrees, improved contact with the punctures 91 is achieved with the dome-shaped heating element 89 as compared with the flat-ended heating element 87.

Figure 8:
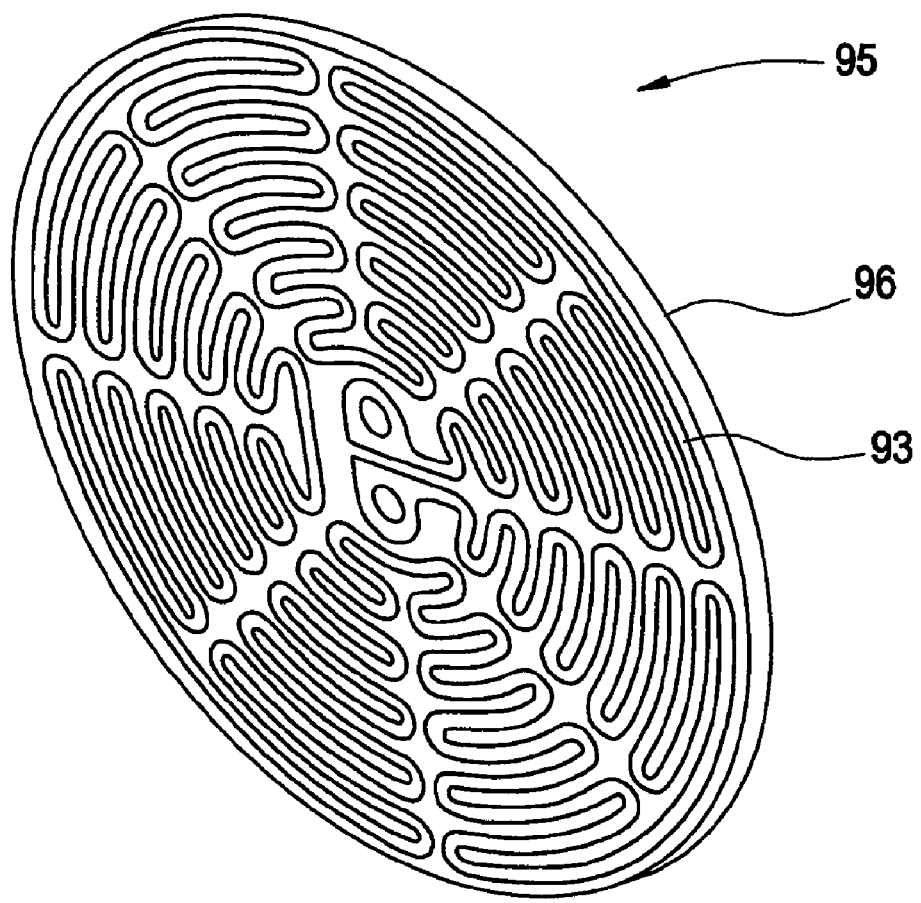
FIG. 8 illustrates an embodiment of an exemplary configuration of a resistance heating component of a heating element.

FIG. 8 shows a resistance heating component 93 of a heating element 95. Conducting elements 93 may have various configurations depending on particular applications. Alternative configurations are possible for creating alternative heating patterns. Conducting elements 93 may be contained or embedded within a layer of material 96 to form a heating element 95. In alternate embodiments, the layer of material 96 may be removed. The material 96 may preferably be silicone or another similar material that is electrically insulating. Alternatively, conducting elements 93 may be sandwiched or compressed between two or more layers of material 96 to form a heating element 95. The sandwiching or compressing may improve the closure abilities of embodiments in accordance with the principles of the invention. The sandwiching or compression may allow heat distribution to improve closure of punctures in vessel walls. The conducting elements 93 may be wires or other similar materials for conducting electricity and generating heat energy. The conducting elements 93 may be metallic or other electrically conductive materials. The various configurations of conducting elements 93 may be customized for particular applications to distribute heat in a desired pattern.

FIGS. 9A-9G illustrate operation of a system 101 for closing a puncture in a vessel wall with an anchoring device 103, a positioning device 105 and a flexible heating element 107. The system 101 may be used with any of the anchoring devices, positioning devices, and/or heating elements as described above. The following description is for illustrative purposes only.

Figure 9A:
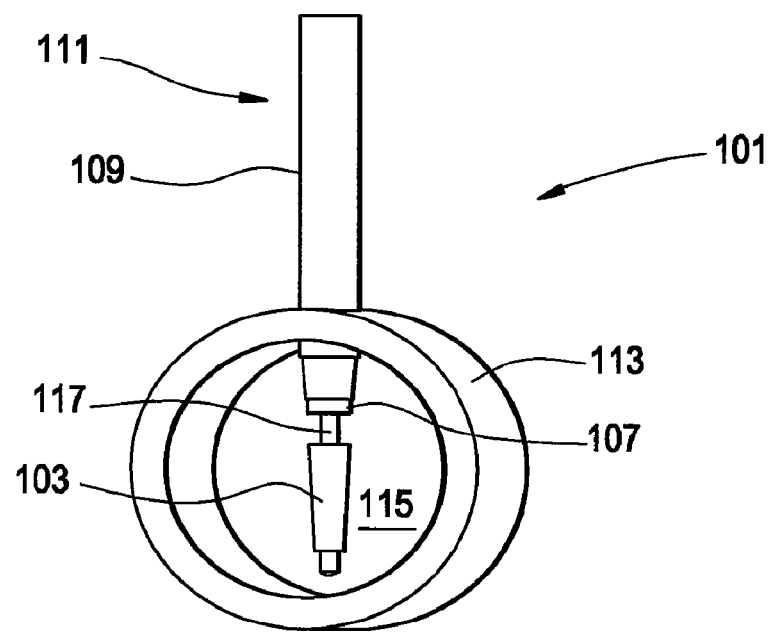
FIGS. 9A-9G illustrate an embodiment of an operation of an apparatus with an anchoring device, a positioning device and a flexible heating element.
Figure 9B:
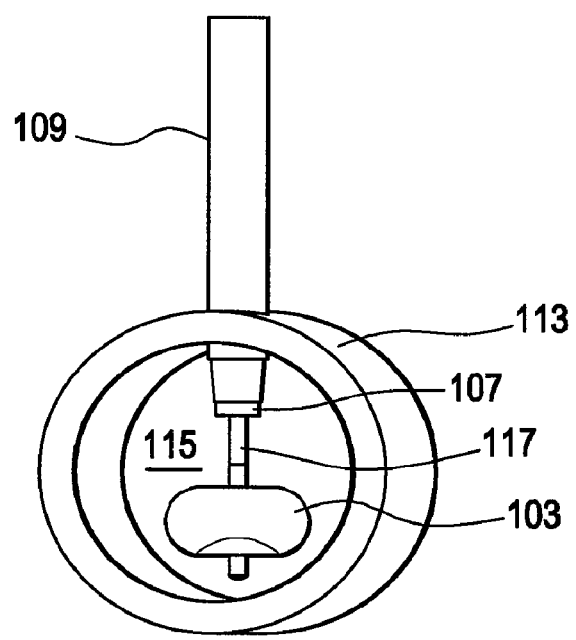
Figure 9C:
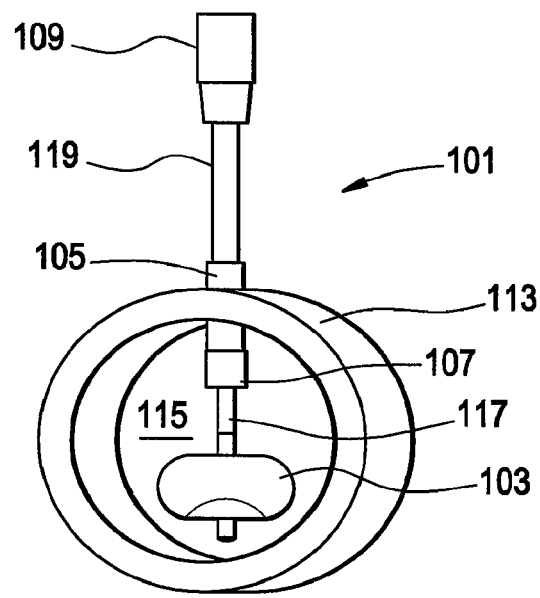

An introducer shaft 109 of an introducer apparatus 111 may be introduced through a vessel wall 113 as shown in FIG. 9A. The introducer apparatus 111 may be used during a therapeutic or diagnostic procedure, such as arterial catheterization. After completion of the therapeutic or diagnostic procedure, an un-deployed anchor 103 operably coupled to a distal end of an anchor shaft 117 may be passed through the introducer shaft 109 and into a vessel lumen 115. A proximal end of the anchor shaft 117 may be in fluid communication with a source of fluid for deploying the anchor 103. Such communication is particularly preferably with the anchor device is a balloon or sponge. The un-deployed anchor 103 may be a balloon or another type of anchor device. A heating element 107 may also be passed through the introducer shaft 109 into the vessel lumen 115. The un-deployed anchor 103 may then be deployed, such as inflated in the case of a balloon anchor device or expanded in the case of an expansible cage or sponge, to a desired size, as shown in FIG. 9B. The introducer shaft 109 may then be withdrawn from the vessel lumen 115, as shown in FIG. 9C. The withdrawal of the introducer shaft 109 from the vessel lumen 115 may expose a heating element shaft 119 and a positioning device 105. The positioning device 105 and the heating element 107 may both be operably in communication with the heating element shaft 119. The positioning device 105 may be a balloon or another type of positioning device. The exposure of the positioning device may result in its deployment, such as may be achieved when an expansible cage positioning device is used and is kept in an un-deployed state by being contained within the introducer shaft 109, or the positioning device may be un-deployed.

Figure 9D:
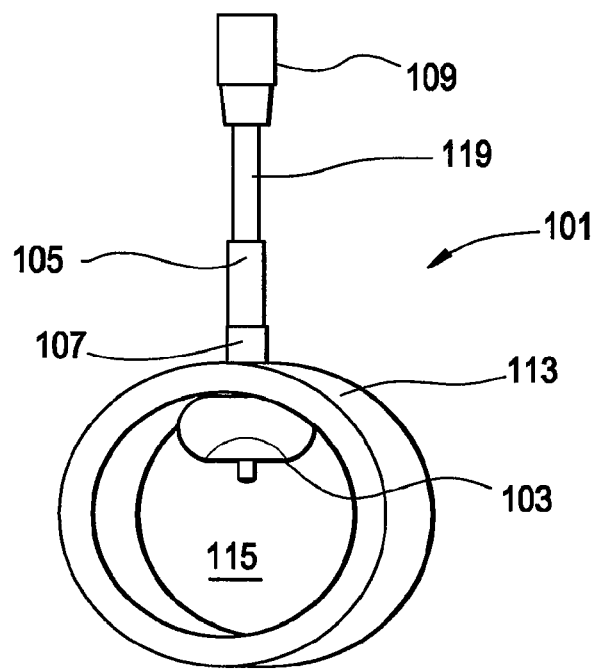
Figure 9E:
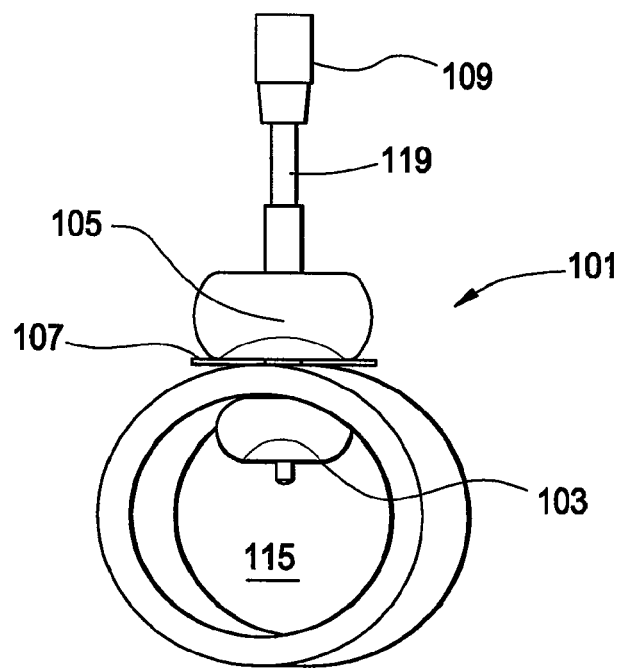
Figure 9F:
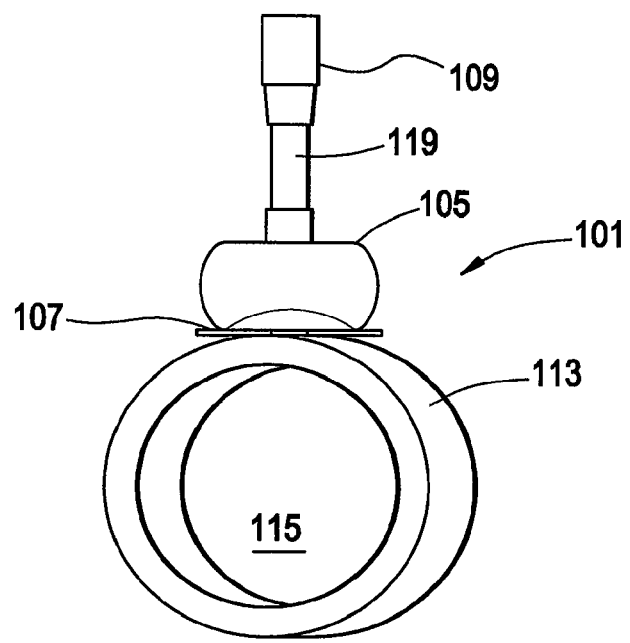
Figure 9G:
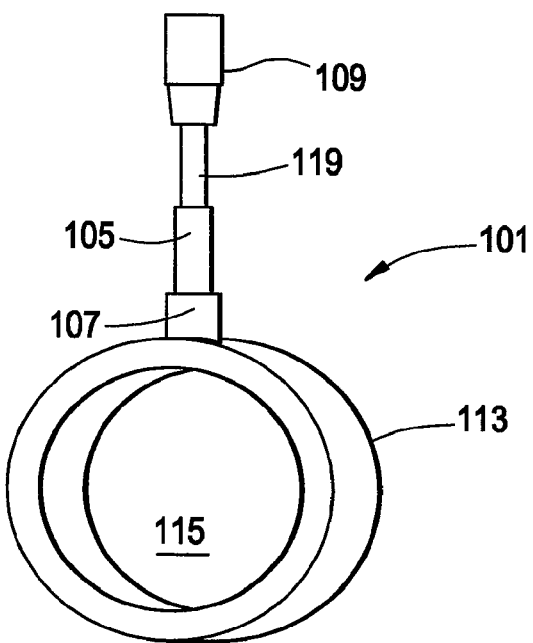

The anchor shaft 117 may be withdrawn from the vessel lumen 115 until the anchor device 103 contacts an inner surface of the vessel wall 113. The positioning device 105 and the heating element may then be located outside of the vessel lumen 115. The positioning device 105 and the heating element 107 may be pushed toward an outer surface of the vessel wall 113 to a predetermined distance from the anchor device 103 as shown in FIG. 9D. The predetermined distance may be determined by the location, configuration and size of the positioning device 105 and/or the heating element 107. A preferred distance may be approximately 1 mm but other preferred distances are possible. The preferred distance may be chosen to sandwich a certain amount of tissue such that heat is conducted uniformly through the tissue to close the puncture. The positioning device 105 may be deployed, such as inflated in the case of a balloon anchor or expanded in the case of an expansible cage or sponge, to a desired size near or in contact with a puncture site, as shown in FIG. 9E. The heating element 107 may be a flexible heating element. The heating element 107 may be folded or wrapped around at least part of the positioning device 105 when the heating element 107 is inserted within the patient. The deployment of the positioning element 105 may cause the flexible heating element 107 to deploy and flatten or conform against the outside surface of the vessel wall 113. The anchor device 103 may be reduced in volume or un-deployed. The reduced anchor device may be withdrawn out of the vessel lumen 115 and through heating element shaft 119, as shown in FIG. 9F. The heating element 107 may then be activated to close a puncture in the vessel wall 113. After the closing is complete, the positioning element 105 may be reduced in volume or un-deployed, as shown in FIG. 9G. The heating element 107 may correspondingly be folded or wrapped around the positioning element 105 in a manner similar to the configuration during insertion of the heating element 107. For example, the heating element 107 may be coupled at one or more point to positioning element 105. Alternatively, the heating element may be actuated by a mechanical actuator (not shown). The system may then be withdrawn from the patient.

Figure 10:
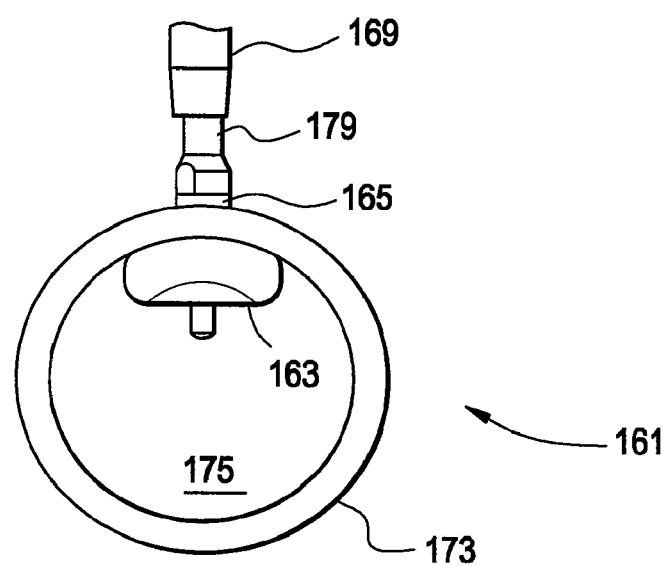
FIG. 10 illustrates an embodiment of an operation of an apparatus with an anchoring device and a rigid heating element.

FIG. 10 illustrates operation of a system 161 for closing a puncture in a vessel wall with an anchoring device 163 and a rigid heating element 165. The system 161 may be used with any of the anchoring devices and/or heating elements as described above. The following description is for illustrative purposes only. The operation of the system 161 is similar to other embodiments described in this specification. Generally, an introducer shaft 169 of an introducer apparatus may be introduced through a vessel wall 173. An un-deployed anchor 163 may be passed through the introducer shaft 169 and into a vessel lumen 175. An un-deployed anchor 163 may be a balloon or another type of anchor device. An un-deployed anchor 163 may then be inflated to a desired size. The introducer shaft 169 may then be withdrawn from the vessel lumen 175. The withdrawal of the introducer shaft 169 may preferably bring the anchor device 163 into contact with an inner surface of the vessel wall 173. The withdrawal of the introducer shaft 169 may expose a rigid heating element 165 on a heating element shaft 179. Alternatively, the rigid heating element 165 may be inserted after withdrawal of the introducer shaft 169 from the vessel lumen 175. The rigid heating element 165 may be flat-ended or dome-shaped. The heating element 165 may be positioned on a distal end of the heating element shaft 179. The heating element shaft 179 may be pushed toward the vessel wall 173 to push the heating element 165 against an outer surface of the vessel wall 173 near a puncture. The heating element 165 may be in direct contact with the vessel wall 173 or may be in close proximity. Preferably, the heating element 165 is a predetermined distance away from the vessel wall 173, such as approximately 1-2 mm, but not within the vessel lumen 175. The anchor device 163 and the heating element 165 may sandwich the vessel wall 173 and any intervening tissue. Any intervening tissue may be compressed between the anchor device 163 and the heating element 165 in a predetermined amount. For example, approximately 1-2 mm may separate the anchor device 163 and the heating element 165. A locking point (not shown in FIG. 10) on the anchor shaft (not shown in FIG. 10) or heating element shaft 179 may ensure the proper distance between the anchor device 163 and the heating element 165. A locking point may provide consistent positioning. The anchor device 163 may be reduced in volume or un-deployed and withdrawn out of the vessel lumen 175 and through heating element shaft 179. The heating element 165 may then be activated to close a puncture in the vessel wall 173.

Alternatively, a first amount of heat may be applied to the vessel wall 173 by the heating element 165. Heat may be applied in an amount sufficient to cause the heating element 165 to "stick" or attach temporarily to the vessel wall 173 and/or intervening tissue, but not permanently bond to the heating element 165. The sufficient amount of heat can be accomplished by way of duration and/or temperature, for example. The heating element 165 may stick without permanently or completely closing the puncture. The heating element 165 may have a non-stick coating, such as silicone, TEFLON, or other similar materials to prevent permanent adhering of the vessel wall 173 and/or intervening tissue to the heating element 165. The first amount of heat may thus allow the heating element 165 to remain in position without the anchor device 163. The anchor device 163 may be withdrawn after the application of the first amount of heat. A second amount of heat may then be applied to the vessel wall 173 and/or intervening tissue by the heating element 165 to close the puncture. The second amount of heat may cause shrinking of the vessel wall 173 and/or intervening tissue such that the puncture is closed. After the closing is complete, the heating element shaft 179 may be withdrawn. This two-stage heating operation may be used with any of the embodiments described herein. Alternatively, a single stage heating operation may be used with any of the embodiments described herein. Furthermore, any number of stages of heating may be provided in accordance with the principles of the invention.

Figure 11:
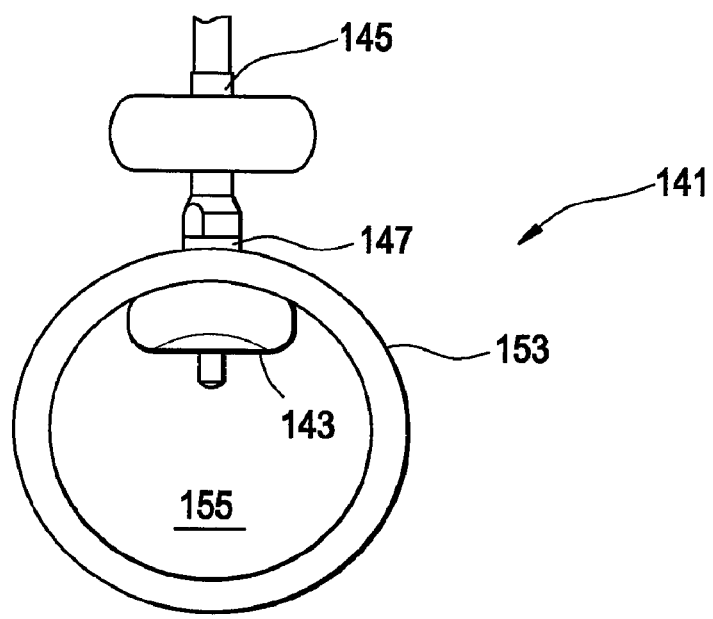
FIG. 11 illustrates an embodiment of an operation of an apparatus with an anchoring device, a positioning device and a rigid heating element.

FIG. 11 illustrates operation of a system 141 for closing a puncture in a vessel wall with an anchoring device 143, a positioning device 145 and a rigid heating element 147. Operation of the system 141 may be similar to operation of the systems as found in other embodiments described herein. The system 141 may be used with any of the anchoring devices, positioning devices, and/or heating elements as described above. The following description is for illustrative purposes only.

An un-deployed anchor device 143 may be passed into a vessel lumen 155. The un-deployed anchor device 143 may be deployed and moved into contact with an inner surface of a vessel wall 153. The positioning device 145 and the heating element 147 may then be outside the vessel wall 153 and the positioning device 145 and the heating element 147 may be pushed toward an outer surface of the vessel wall 153 until the heating element 147 is near or contacts the vessel wall 153 near or contacting a puncture. The positioning device 145 may be deployed above the puncture site. The heating element 147 may be a rigid, flat-ended heating element or any other suitable heating element. The anchor device 143 may be reduced in volume or un-deployed. The reduced anchor device 143 may be withdrawn out of the vessel lumen 155. The heating element 147 may then be activated to close a puncture in the vessel wall 153. Alternatively, the heating element 147 may be activated in a two-stage heating operation, with the anchor device 143 being withdrawn between the two stages. After the closing is complete, the positioning device 145 may be reduced in volume or un-deployed. The system may then be withdrawn from the patient.

Figure 12:
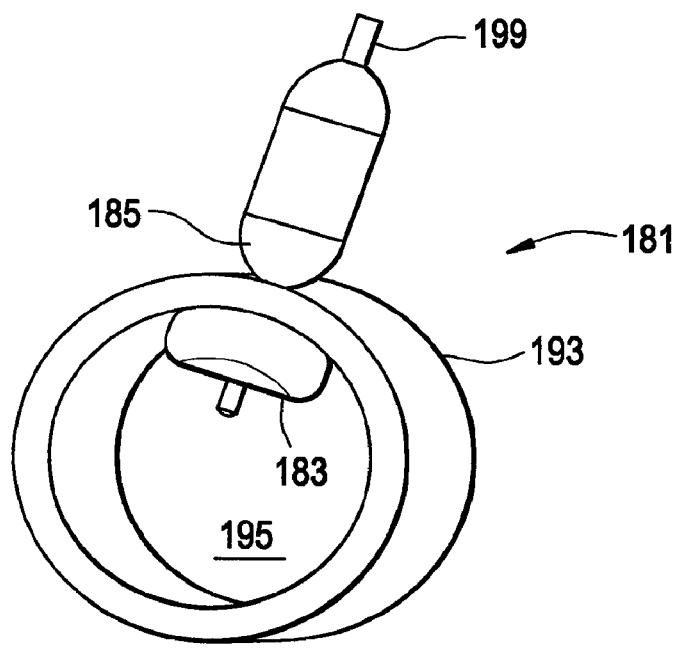
FIG. 12 illustrates an embodiment of an operation of an apparatus with an anchoring device and a rigid, over-the-wire heating element.

FIG. 12 illustrates operation of a system 181 for closing a puncture in a vessel wall with an anchoring device 183 and a rigid, over-the-wire heating element 185. In an over-the-wire configuration, the heating element 185 may pass over an anchor shaft (not shown in FIG. 12). The heating element 185 may have a lumen from a distal end to a proximal end. The heating element 185 may be threaded over the anchor shaft with the heating element 185 moveable along the length of the anchor shaft. The system 181 may be used with any of the anchoring devices and/or heating elements as described above. The system 181 operates in a similar manner to other embodiments described herein.

An un-deployed anchor device 183 may be inserted into a vessel lumen 195. The anchor device 183 may be deployed and moved into contact with an inner surface of a vessel wall 193. A heating element shaft 199 may be coupled to a heating element 185 with the heating element 185 at a distal end of the heat element shaft 199. The heating element 185 may preferably be a rigid, dome-shaped heating element but could be any configuration suitable for a particular application. A dome-shaped heating element may increase contact with the vessel wall, as compared to flat heating elements and may force tissue to comport with the contours of the heating element. A preferred dome-shaped heating element may generally be a spherical shape with a flattened distal end. The heating element shaft 199 may be inserted over an anchor shaft (not shown) in an over-the-wire configuration until contacting an outer surface of the vessel wall 193 above a puncture. The heating element 185 may be activated in a single or two-stage heating operation. When closing is complete and the anchor device 183 is un-deployed, the system may be withdrawn from the patient.

Figure 13A:
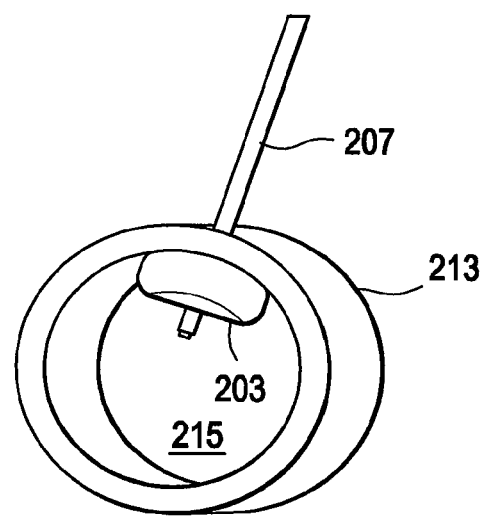
FIGS. 13A-13F illustrate an embodiment of an operation of an apparatus with an anchoring device and a rigid, split heating element.
Figure 13B:
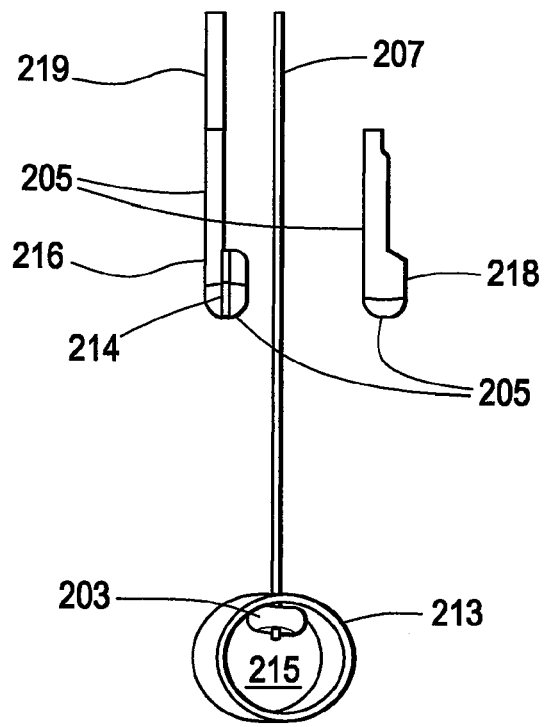
Figure 13C:
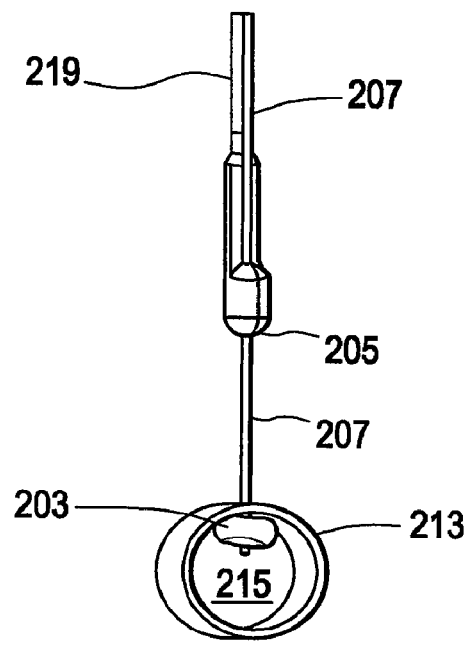
Figure 13D:
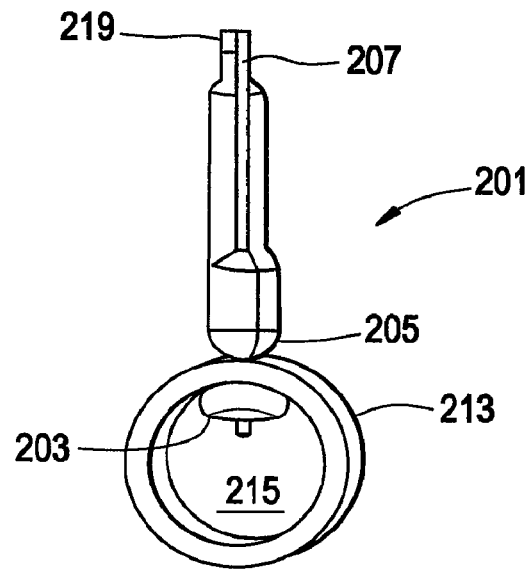
Figure 13E:
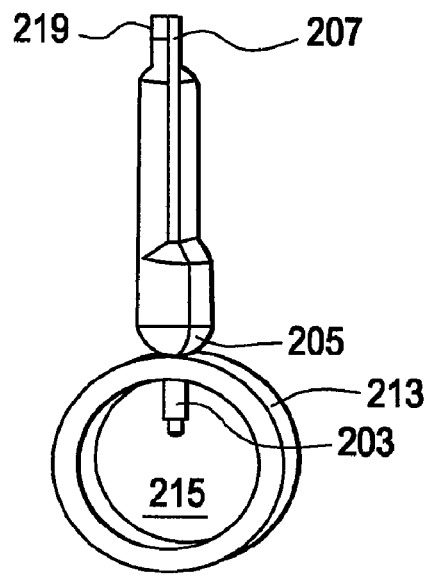
Figure 13F:
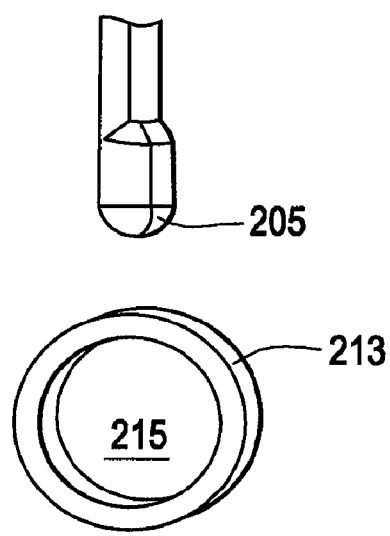

FIGS. 13A-13F illustrate operation of a system for closing a puncture in a vessel wall with an anchoring device 203 and a rigid, split heating element 205. An un-deployed anchor 203 may be passed through a vessel wall 213 and may be deployed to a desired size within a vessel lumen 215 as shown in FIG. 13A. A heating element shaft 219 may be coupled to a heating element 205 with the heating element 205 at a distal end of the heating element shaft 219. The heating element 205 may preferably be a dome-shaped heating element but could be any configuration suitable for a particular application. The heating element 205 may be a split heating element with individual pieces that connect to form a complete heat element 205. In a preferred embodiment, a first heating element adapter 216 is coupled to or integrated with the heating element shaft 219. Another heating element adapter 218 may be coupled to the first individual piece to form a complete heating element 205. One or both of the heating element adapters 216, 218 may have a notch or groove 214 for accepting the anchor shaft 207. The heating element adapters 216, 218 may be placed surrounding the anchor shaft 207 as shown in FIG. 13B. The anchor shaft 207 may be lead through a notch 214 in the heating element adaptors 216, 218. The heating element 205 may be closed over the anchor shaft 207 as shown in FIG. 13C. The closing may be accomplished through corresponding male and female components or other similar systems. At least one of the heating element adapters 216, 218 may be coupled to the heating element shaft 219. The heating element shaft 219 may be adjacent to and slide coaxially with the anchor shaft 207 in an over-the-wire configuration. The heating element shaft 219 may be moved distally until the heating element 205 contacts an outer surface of the vessel wall 213 near or in contact with a puncture as shown in FIG. 13D. The anchor device 203 may be reduced in volume or un-deployed, as shown in FIG. 13E. The reduced anchor device 203 may be withdrawn out of the vessel lumen 215 and through heating element shaft 219. The heating element 205 may then be activated to close a puncture in the vessel wall 213. After the closing is complete, the heating element shaft 219 and heating element 205 may be withdrawn as shown in FIG. 13F.

FIGS. 14A-14H illustrate a floating anchor 477. The floating anchor 477 may be used with any of the embodiments described in this application.

Figure 14A:
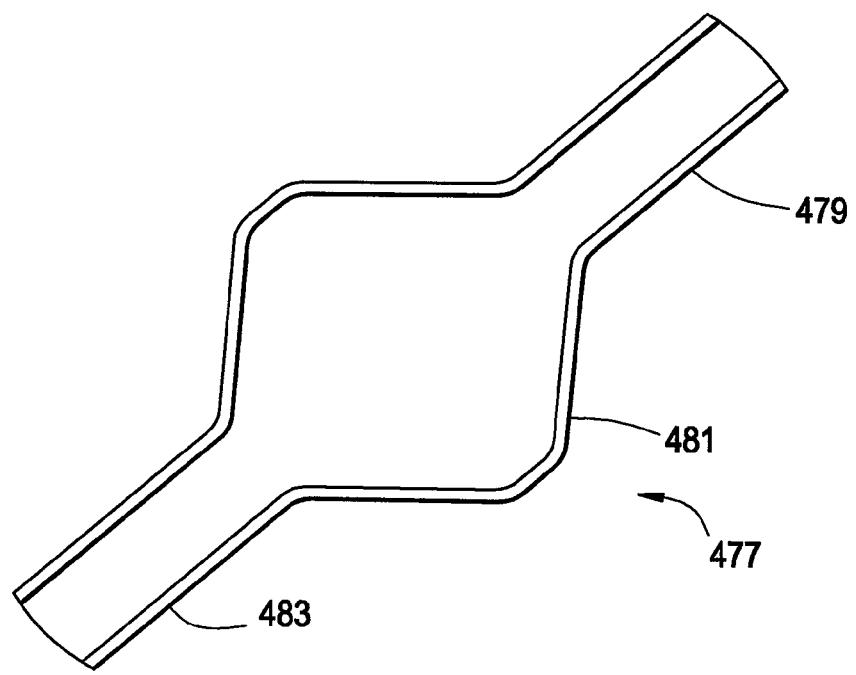
FIGS. 14A-14H illustrate an embodiment of a floating anchor.
Figure 14B:
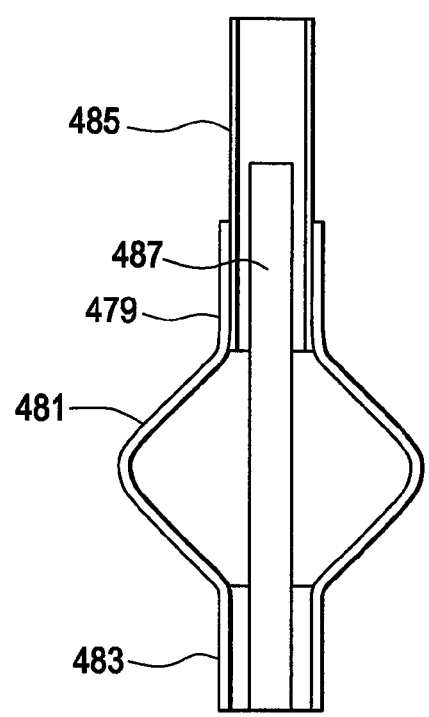
Figure 14C:
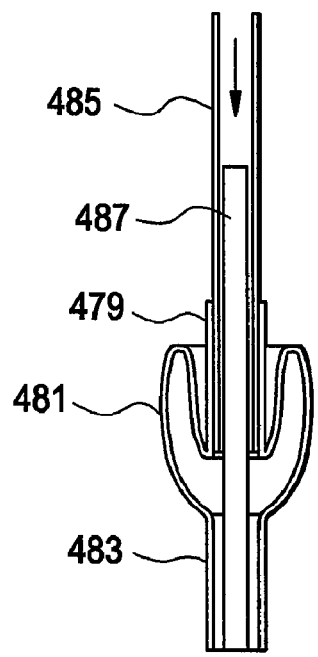
Figure 14D:
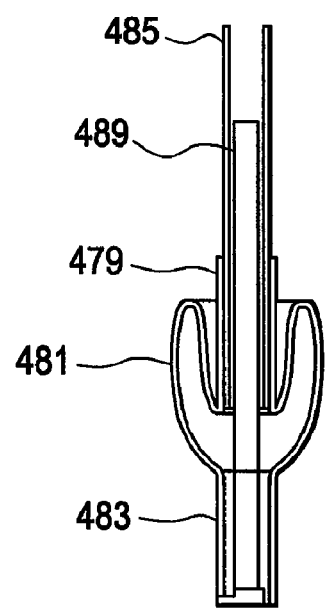
Figure 14E:
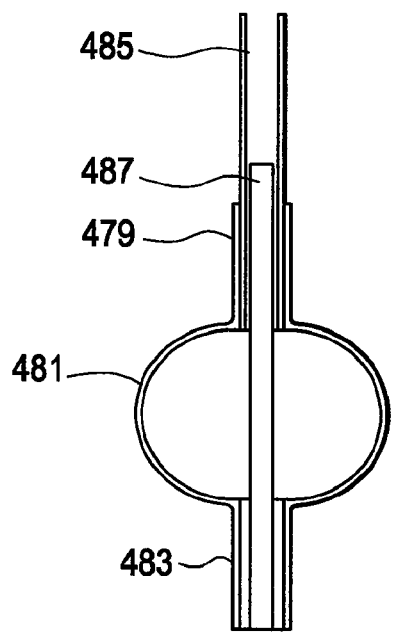
Figure 14F:
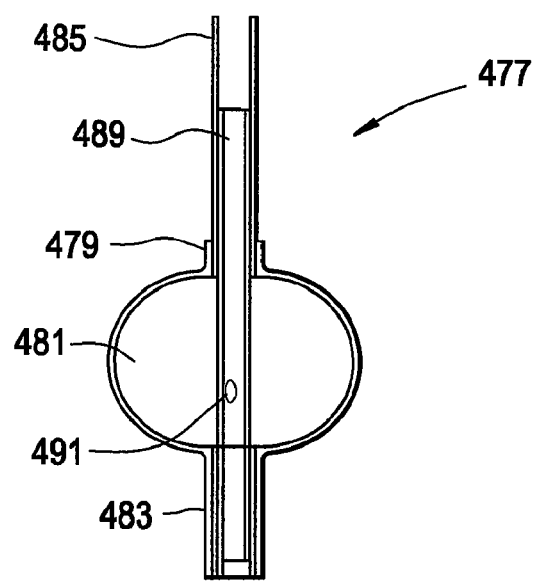

As shown in FIG. 14A, the floating anchor 477 may include a proximate neck 479, a main inflatable anchor body 481, and a distal neck 483. A shaft 485, as shown in FIG. 14B, may be glued or otherwise adhered to the proximate neck 479 of the floating anchor 477. A rod 487 may be glued or otherwise adhered to the distal neck 483 of the floating anchor 477. The rod 487 may be configured to readily slide within the shaft 485, as shown in FIG. 14B. As shown in FIGS. 14C and 14D, the main inflatable anchor body 481 may fold over itself as the shaft 485 is pushed downward such that the proximate neck 479 is involuted into the main inflatable anchor body 481. The proximate neck 479 may move toward the distal neck 483 while the rod 487 is sliding inside the shaft 485, as shown in FIGS. 14C and 14D. The rod 487 of FIG. 14C may be replaced with a tube 489, as shown in FIG. 14D. The distal neck 483 may move away from the proximate neck 479 during inflation of the main inflatable anchor body 481, pulling the rod 487 with the distal neck 483. The rod 487 or tube 489 preferably keeps the proximate neck 479 and the distal neck 483 parallel, as shown in FIGS. 14E and 14F, respectfully. A gap between the shaft 485 and the rod 487 preferably is sufficient to allow fluid to flow and inflate the main inflatable anchor body 481, as shown in FIG. 14E. The fluid may flow through the shaft 485. Alternatively, where the rod 487 is replaced with a tube 489, as shown in FIG. 14F, the gap between the tube 489 and the shaft 485 may be smaller than the gap of FIG. 14E. One or more holes 491 in a wall of the tube 489 may enable fluid to flow through the tube 489 and inflate the main inflatable anchor body 481, as shown in FIG. 14F. Fluid may flow through the shaft 485 and into the tube 489.

Figure 14G:
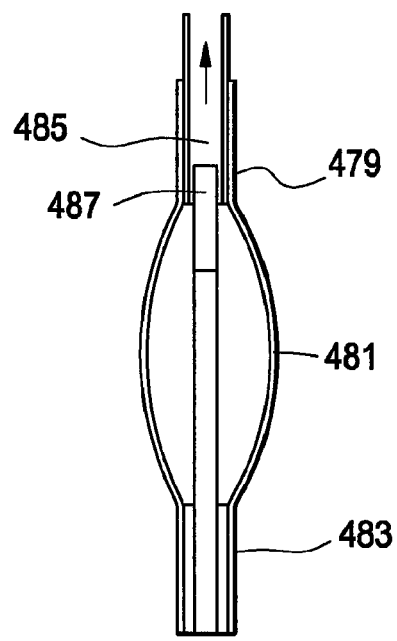
Figure 14H:
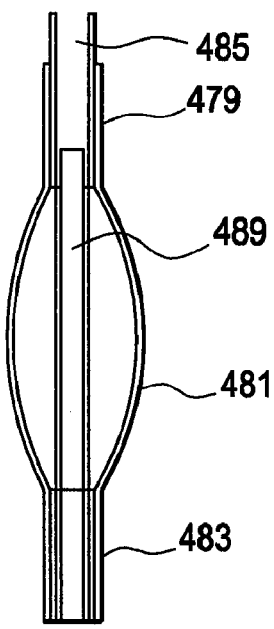

The floating anchor 477 may be used with any of the positioning devices and/or heating elements described above. The floating anchor 477 would be deployed in a vessel lumen, that the main inflatable anchor body 481 may be moved proximally into contact a puncture at an inside wall of a vessel. After the floating anchor 477 is used, such as in a system for closing a puncture in a vessel wall described herein, the main inflatable anchor body 481 may be deflated by pulling the shaft 485 away from a vessel wall, as shown in FIGS. 14G and 14H The shaft 485 may be pulled to deflate the inflatable anchor body 481 such that when the inflatable anchor body 481 deflates to a certain diameter the inflatable anchor body 481 may be withdrawn through the puncture and removed from the patient. The proximal neck 479 may move away from the distal neck 483 to elongate and minimize the horizontal profile of the main inflatable anchor body 481, as shown in FIGS. 14G and 14H. A tip of the rod 487, as shown in FIG. 14G or the tube 489, as shown in FIG. 14H, may remain within the shaft 485 to keep the proximate neck 479 and the distal neck 483 parallel.

Figure 15:
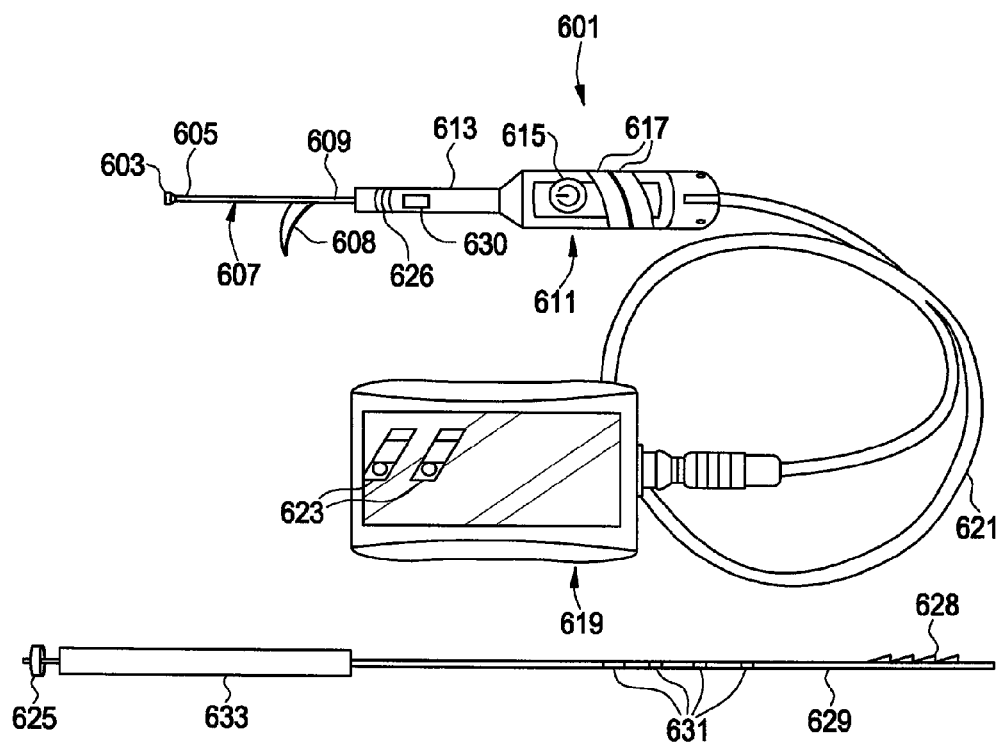
FIG. 15 is an embodiment of an exemplary system for closing a puncture in a vessel wall including a system for closing a puncture in a vessel wall.

FIG. 15 is an exemplary system 601 for closing a puncture in a vessel wall. A heating element 603 may be disposed on a distal end 605 of a heating element shaft 607. A proximal end 609 of the heating element shaft 607 may be coupled to a handheld unit 611. The handheld unit 611 may have a grip 613, a power button 615, other inputs 617 and other controls. The handheld unit 611 may be coupled to a power supply unit 619 by a connecting cable 621. The power supply unit 619 may have one or more indicators 623 of system status.

An anchor device 625 may be provided on a distal end of an anchor shaft 629. The anchor shaft 629 may have one or more indicators 631 for determining position of the anchor 625 within a patient. The one or more indicators 631 may show the position of the heating element 603 relative to the anchor device 625. A user may employ a visual reference to identify when the heating element 603 is in a proper position relative to the anchor device 625. In a preferred embodiment, a predetermined indicator 631 may indicate that the heating element 603 is 1 mm, for example, or another preferred distance from the anchor device 625. Other types of arrangements in accordance with the principles of the invention can be used to accomplish a desired fixed distance between an anchor device inside the vessel and a heating element outside the vessel thereby sandwiching the vessel wall between the anchor device and the heating element.

A trigger 608 may be used to lock the heating element 603 in a position relative to an anchor device 625. The heating element 603 on the heating element shaft 607 may slide coaxially over the anchor shaft 629 to position the heating element 603 relative to the anchor device 625. Preferably, the heating element 603 and the anchor device 625 are a predetermined distance apart, such as approximately 1 mm. The trigger 608 may be activated based upon a user visually inspecting the position of one or more indicators 631 on the anchor shaft 629 relative to the location of the heating element shaft 607. The activation of the trigger 608 may lock relative position of the heating element 603 and the anchor device 625. The heating element shaft 607 may have a reference point that indicates a correct positioning of the heating element 603 relative to the anchor device 625. Alternatively, the trigger 608 may initially be in a locked position. The trigger 608 may then be activated to allow relative movement of the heating element 603 and the anchor device 625. This may allow maneuvering of the heating element 603 relative to the anchor 625 while the trigger 608 is activated. Releasing the trigger 608 may lock the relative position of the elements.

A roll 633 may also be disposed at a predetermined distance from the anchor device 625 on the anchor shaft 629. The roll 633 generally facilitates movement of the heating element 603 through tissue as described below. The roll 633 may preferably have a diameter of less than approximately 2.0 mm when used with a 6 Fr introducer shaft. Other combinations of diameters are possible. The roll 633 may preferably have a thickness of approximately 0.1 mm or another minimal thickness in relation to the diameter of the roll 633. Thickness of the roll 633 is preferably minimized, but retains enough strength to prevent tearing of the roll material during operation.

A first ratchet system 626 may be disposed on the handheld unit 611. The first ratchet system 626 may interact with second ratchet system 628 on the anchor shaft 629. Together, the ratchet systems 626, 629 may provide for one way anchor removal locking. One way anchor removal locking may allow the anchor to move toward the handheld unit 611, but not away from the handheld unit 611. This may prevent the anchor device 625 from moving away from the puncture within the vessel lumen. A button release 630 may be provided to unlock the ratchet system. Placement of the anchor device 62 and heating element 603 a desired position relative to one another may be accomplished using one or more indicators 631, tactile sensations, or other methods of determining the relative positions of the anchor device 625 and the heating element 603.

Figure 16A:
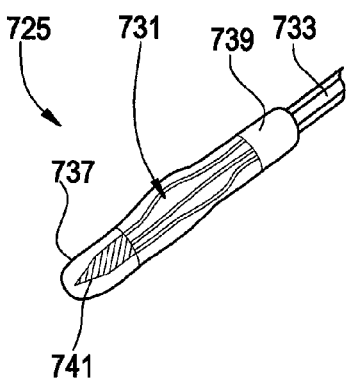
FIGS. 16A-16C illustrate an embodiment of a nitinol anchor surrounded by a coating.
Figure 16B:
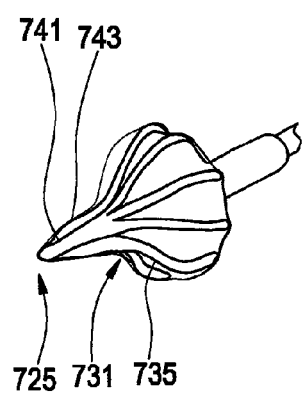
Figure 16C:
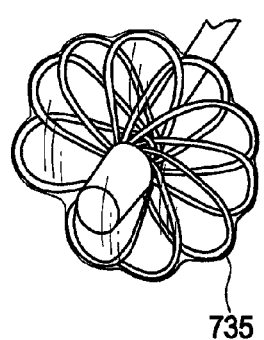

In an embodiment of the present invention, an anchor device 725 may be a nitinol cage 731 as shown in FIGS. 16A-16C The nitinol cage 731 may initially be in an undeployed position, where the nitinol cage may be close to an anchor shaft 733, as shown in FIG. 16A. The one or more prongs 735 may be held in position by a distal positioner 737 at a distal end and a proximal positioner 739 at a proximal end. A distal tip 741 may protrude from the distal end of the nitinol cage 731. The nitinol cage 731 may begin to expand as shown in FIG. 16B. The expansion may be started by releasing tension on one or more prongs 735 forming the nitinol cage 731. The tension may be released by a user actuating the anchor shaft 733 to move the proximal positioner 739 towards the distal positioner 737. Alternatively, once the nitinol cage 731 is within the vessel lumen, the one or more prongs 735 may automatically expand due to the properties of shape-memory materials. FIG. 16C shows the nitinol cage 731 further expanded. Once the nitinol cage is expanded, the nitinol cage 731 may create a relatively planar, circular form. The nitinol cage 731 may have a deployed diameter of approximately 4-7 mm and may have an unexpanded diameter of approximately 1-1.3 mm. The dimensions of the nitinol cage 731 may be adjusted based upon the dimensions of a vessel lumen. If the nitinol cage 731 is too large relative to the inner diameter of the vessel lumen, the nitinol cage 731 may become stuck when being positioned within the vessel lumen, such as when being moved toward a puncture in the vessel wall. If the nitinol cage 731 is too small relative to the inner diameter of the vessel lumen, the nitinol cage 731 may lip out of the puncture.

The nitinol cage 731 may be surrounded with a coating material 743 to prevent passage of blood from a vessel lumen into a puncture in a vessel wall when the nitinol cage 731 is pulled against an inner surface of the vessel wall at the site of the puncture. The coating 743 may be silicone, latex, polyurethane, rubber, rubber-like materials, and/or hyper elastic materials. Preferably, the coating 743 may be made of a material with average strain values between about 600-1000 to accommodate the expansion. Silicone may be preferred for particular embodiments because the strain of silicone may range up to about 1200. The coating 743 preferably allows repeated expansion and contraction without losing elastic performance. Hyperelastic materials may preferably be used to cover the nitinol cage 731 because the nitinol cage 731 may expand from approximately 1 mm to approximately 5-6 mm in a single axis. The coating 743 may form a membrane over the nitinol cage 731. The coating 743 may also prevent injury to tissue and/or the vessel during insertion, expansion, contraction, and/or removal of the nitinol cage 731.

Figure 17B:
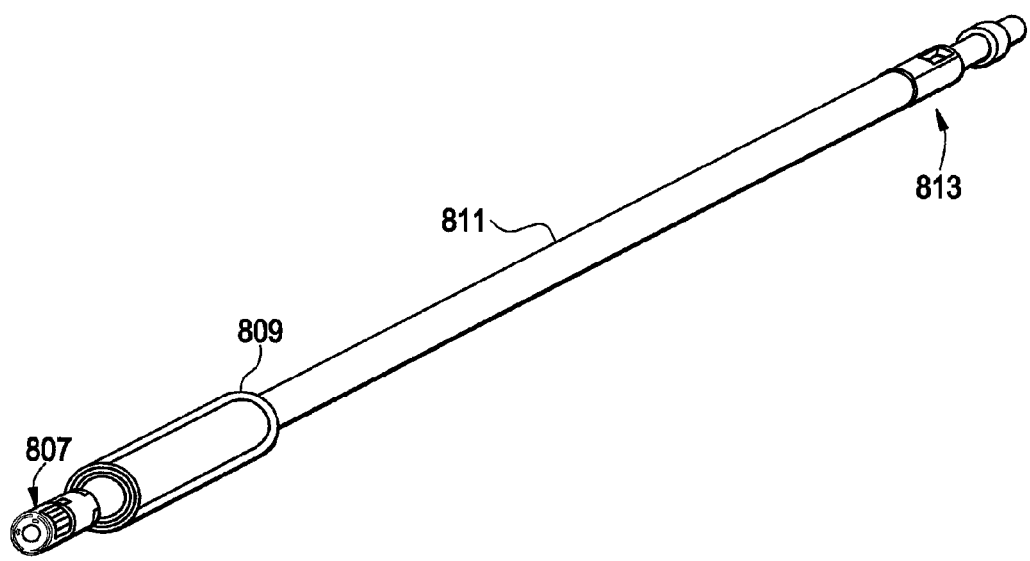
FIGS. 17A-17N illustrate an embodiment of an operation of an apparatus with an anchoring device, heating element and roll.
Figure 17C:
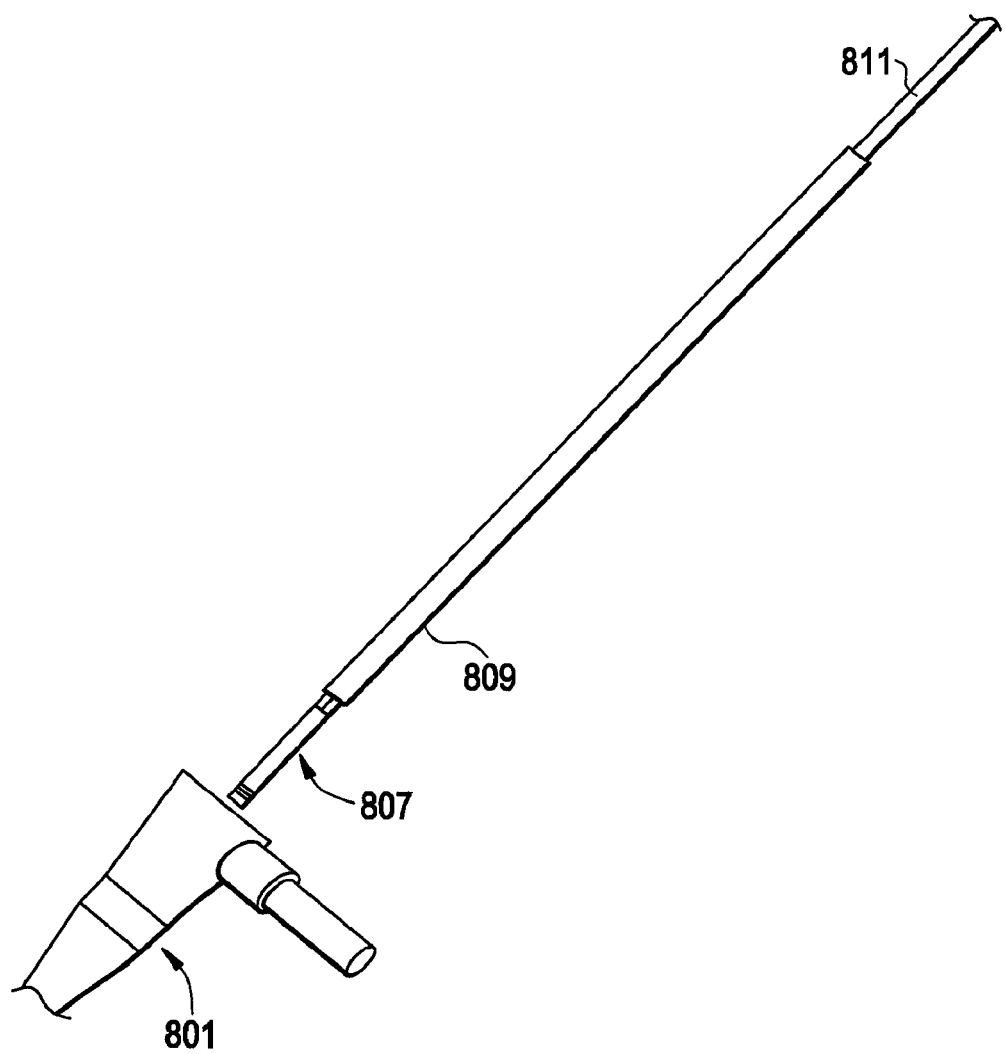
Figure 17D:
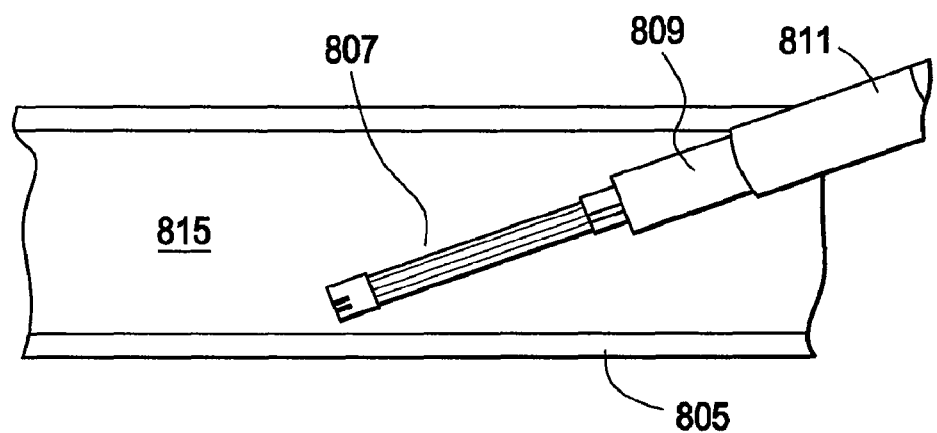
Figure 17E:
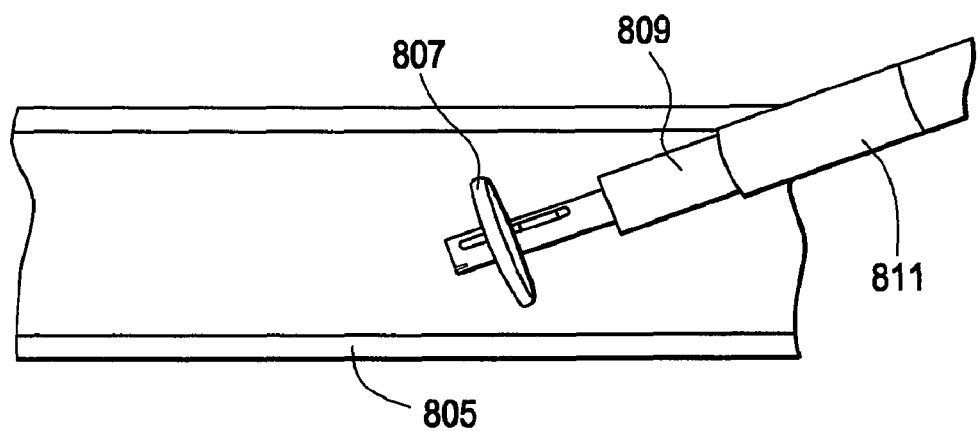
Figure 17F:
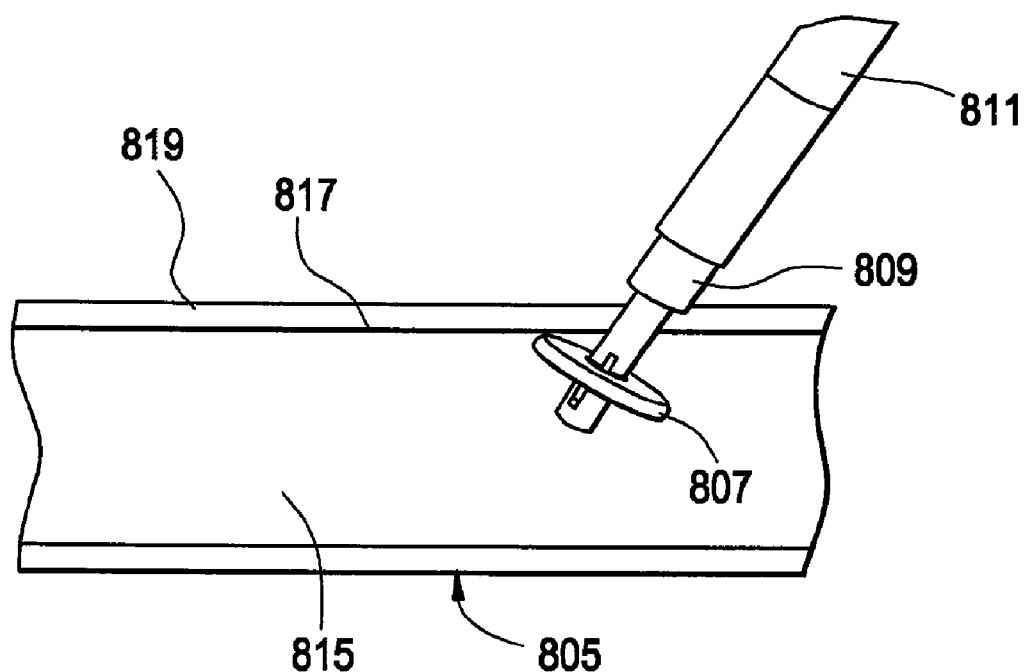
Figure 17G:
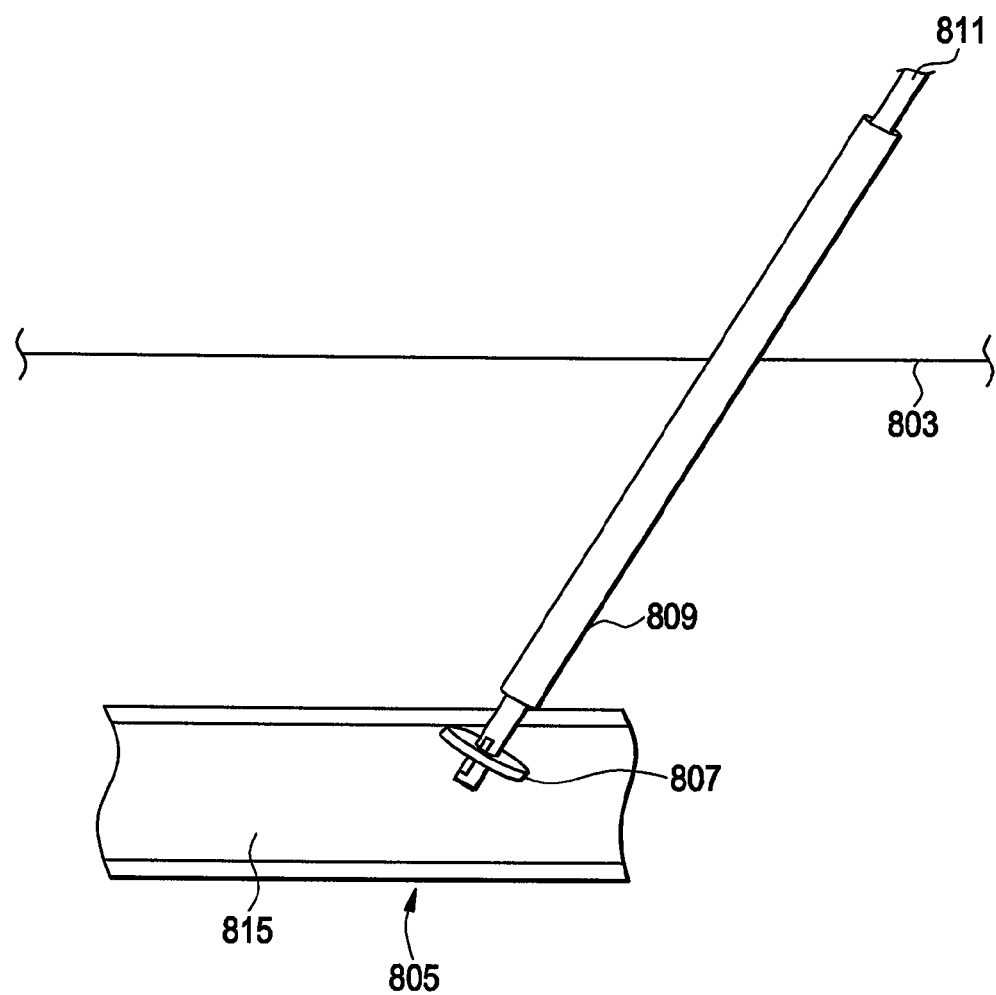
Figure 17H:
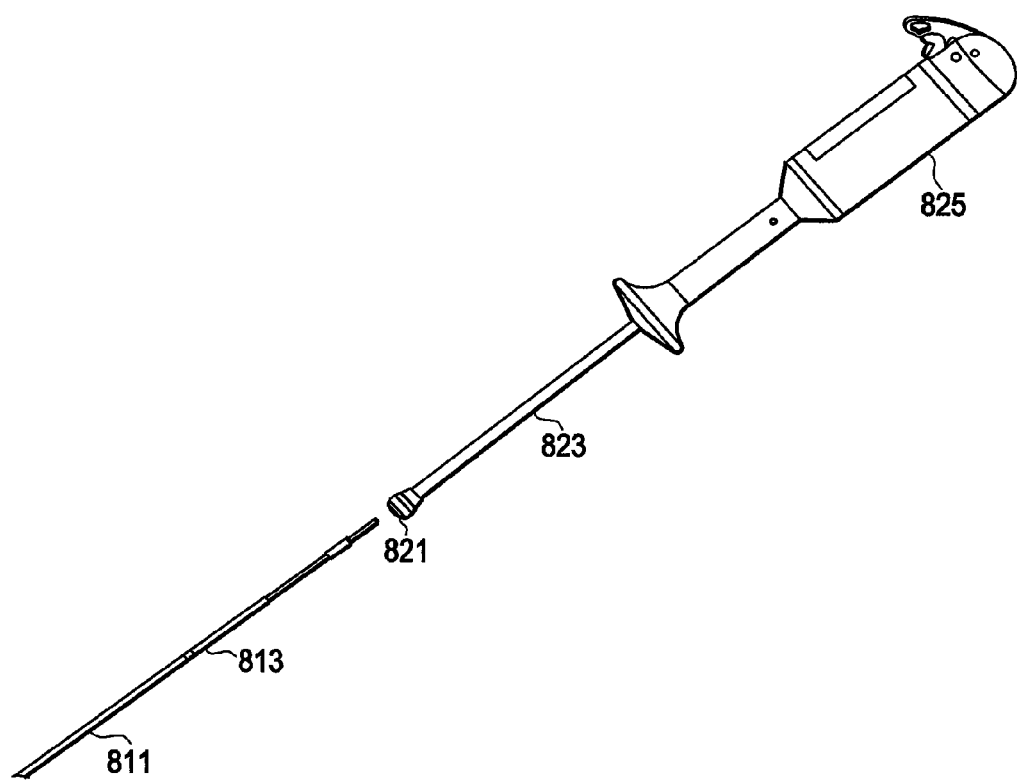
Figure 17I:
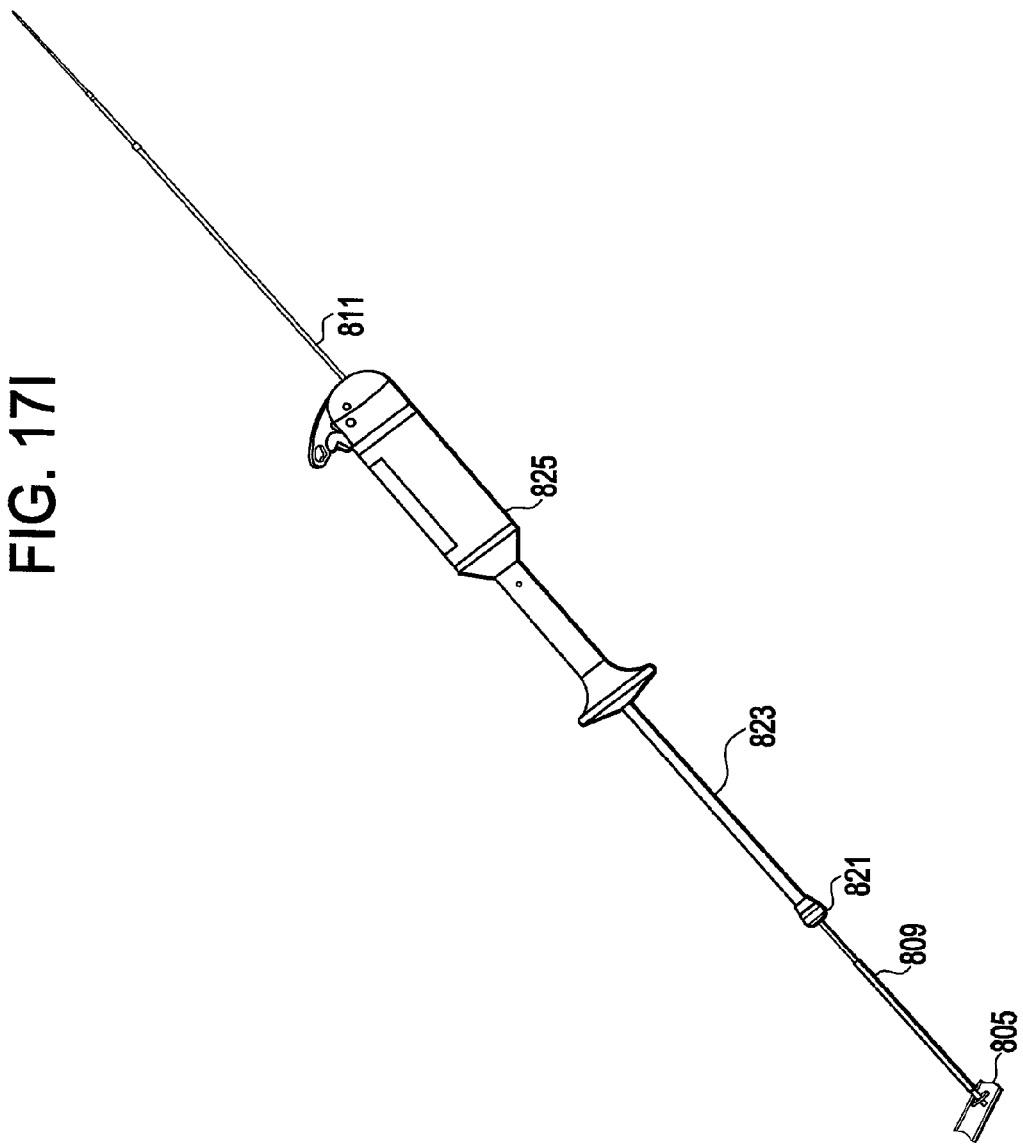
Figure 17J:
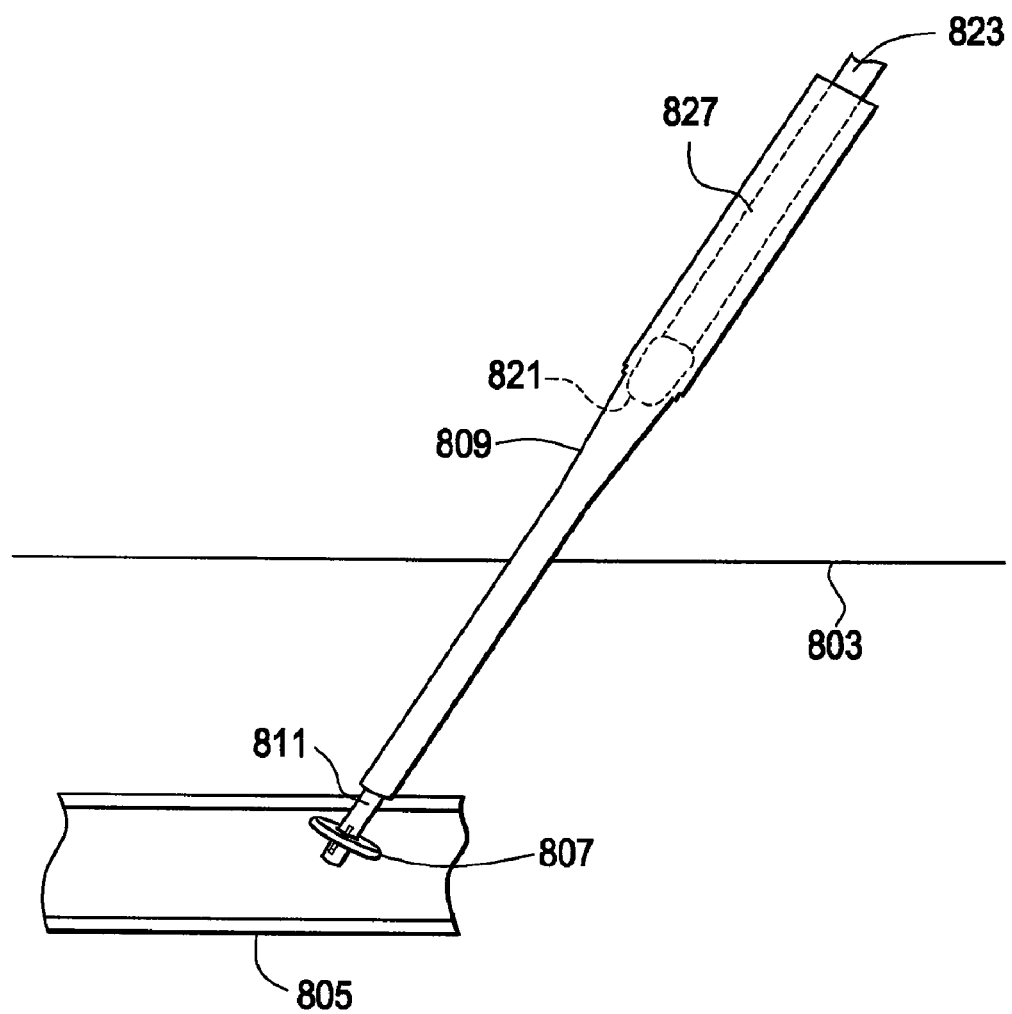
Figure 17K:
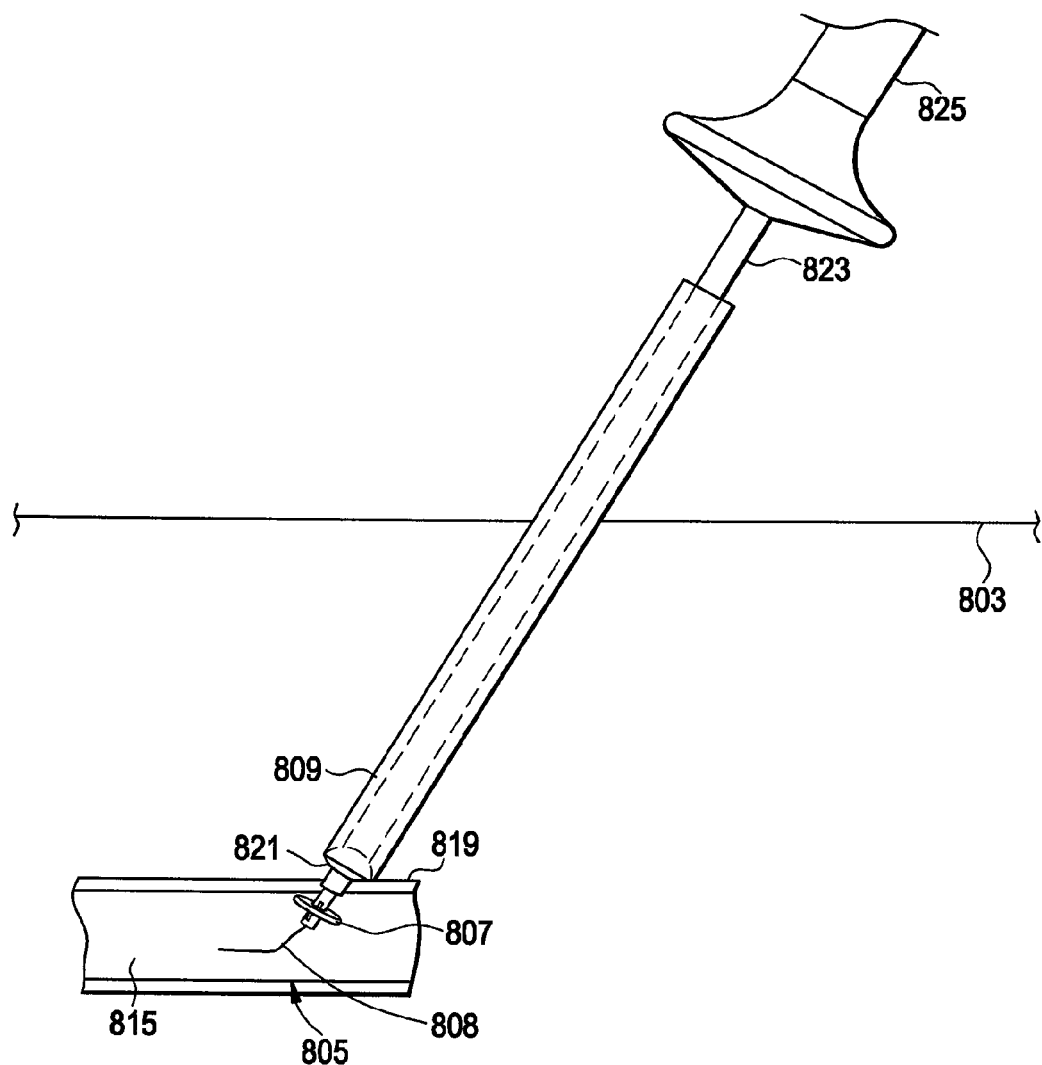
Figure 17L:
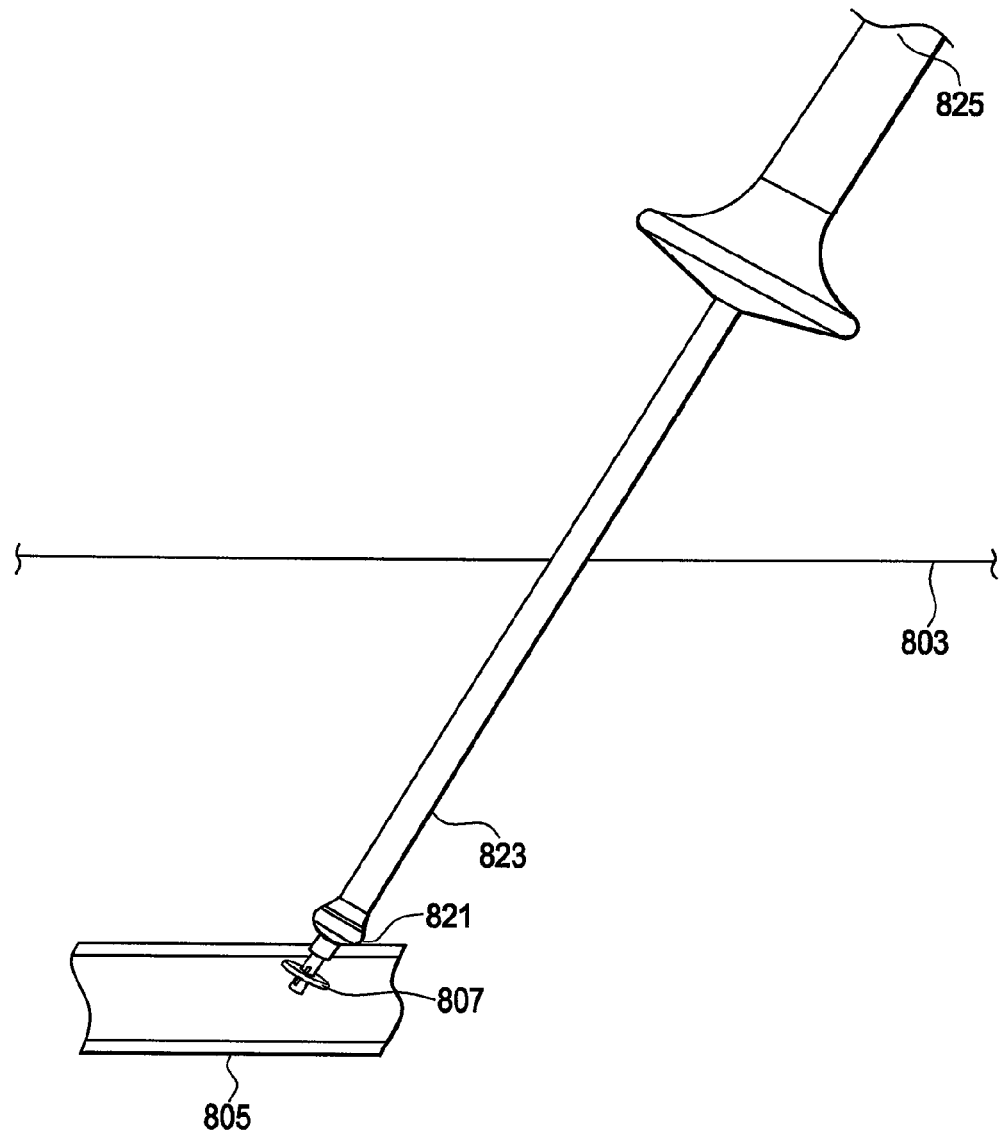
Figure 17M:
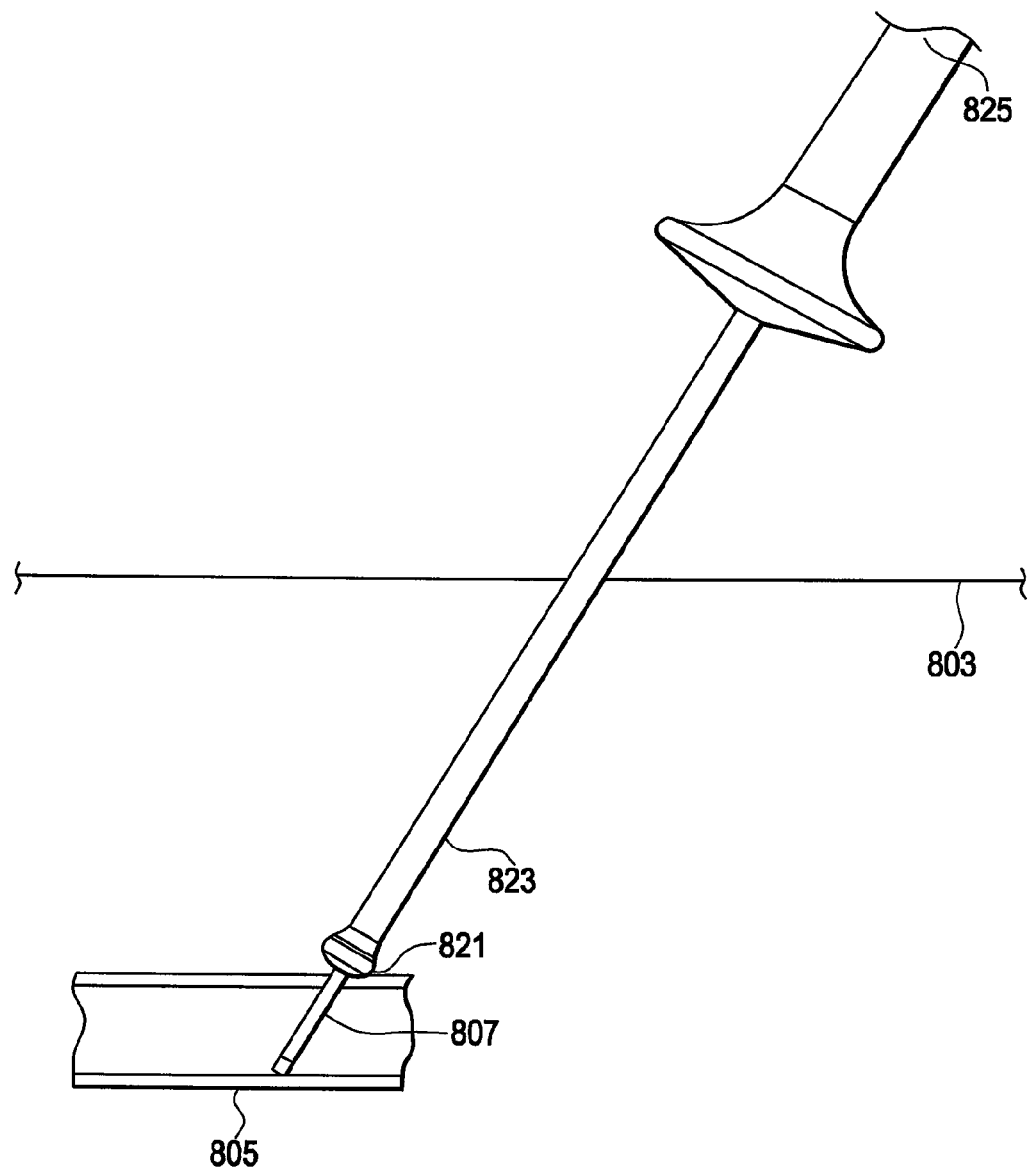
Figure 17N:
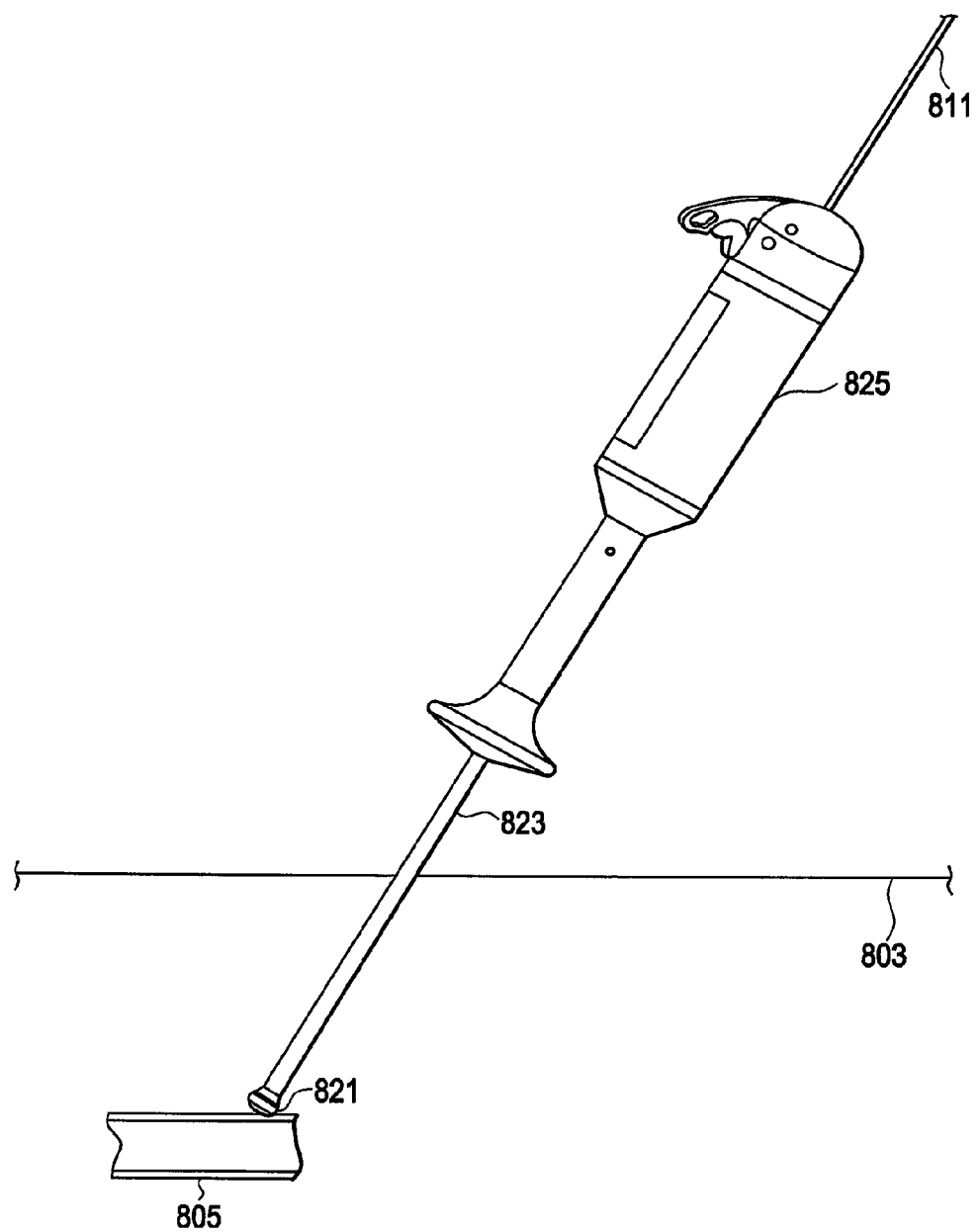

FIGS. 17A-17N show operation of a system for closing a puncture in a vessel wall with an anchoring device, a heating element and a roll. A roll is described herein for reference, but other methods of facilitating movement of the heating element through tissue may be used, if anything. It is contemplated that nothing additional may be needed to facilitate movement of the heating element through the tissue and/or that the heating element configuration alone could accomplish that. For example, a dilator may be used to push a heating element through tissue. The heating element may be coupled to or associated with the dilator. The combined apparatus may be pushed through tissue until the heating element is in a desired position, for example, approximately 1-2 mm from a puncture site. The roll or dilator may be useful for pushing the heating element through tough tissue, scar tissue, etc. The dilator may pass over an anchor shaft and then be removed after positioning of the heating element.

A roll or dilator element may be used with any embodiment described herein. Alternatively, a roll or dilator element may be eliminated altogether in any embodiment described herein.

FIG. 17A shows an introducer sheath 801 inserted through a skin line 803 of a patient and into a vessel 805. The introducer sheath 801 may be or may have been used during a therapeutic or diagnostic procedure, such as arterial catheterization, performed on the patient.

FIG. 17B shows an exemplary anchor device 807 with a roll 809, which is optional. The anchor device 807 may be operably coupled to a distal end of an anchor shaft 811. The roll 809 may be coupled to the anchor shaft 811 at a predetermined distance from the anchor 807. A deployment mechanism 813 may be disposed on the anchor shaft 811 proximally in relation to the roll 809.

The roll 809 may at least partially surround the anchor shaft 811 and preferably completely surrounds the anchor shaft 811 to form a cylindrical structure. The roll 809 is preferably made of PTFE, but may be made of any similarly suitable material that may avoid tearing during insertion of a heating element, as shown in FIG. 17H and may not stick to tissue. The roll 809 may be about 40 to about 100 mm in length. The roll 809 may be attached to the anchor shaft 811 such that when an anchor device 807 is pulled against an inner surface of the vessel 805, the roll 809 is not located within a vessel lumen. Preferably, the roll 809 may be attached approximately 1.5 mm above the proximal side of the anchor device 807. A distal end of the roll 809 may be welded, glued, mechanically coupled or otherwise attached to an anchor shaft 811 at a predetermined distance above the anchor 807. Holes may be drilled through the roll 809. Adhesive may be added to the holes, and the roll 809 may be surrounded by two layers of another sheet material. The additional sheet material may be any material capable of being coupled to the anchor shaft 811 by welding, gluing, mechanical coupling, etc. The adhesive in the holes may bond the two layers of sheet material to one another through the holes, thus securing the roll 809 between the two layers of sheet materials. The inner layer of sheet materials may then be bonded to the anchor shaft 811. The roll 809 may or may not completely encompass the anchor shaft 811.

A slit (not shown) may be present along one or more portions of the roll 809. The slit may allow the roll 809 to expand and may allow passage of a heating element 821, as shown in FIG. 17H through the roll 809. Alternatively, the roll 809 may be made of a material that may expand to accept and allow passage of the heating element 821 through the roll 809. The roll 809 may be expandable to cover the entire diameter of the heating element 821. The roll 809 may allow the heating element 821 to penetrate the subcutaneous tissue by reducing friction. The roll 809 may offer less resistance to movement of the heating element 821 than tissue. The roll 809 may not dilate the tissue as the heating element 821 passes. The roll 809 may be inserted into the patient with the anchor shaft 811.

FIG. 17C shows the anchor device 807 being inserted into the introducer sheath 801. FIG. 17D is a detail of the distal end of the system within the vessel 805. The roll 809 may partially emerge from the introducer sheath 801 within the vessel 805. The anchor device 807 may initially be in an un-deployed state. The un-deployed anchor device 807 may be a nitinol cage, sponge, balloon or another type of anchor device.

The anchor shaft 811 may be inserted into the patient through the introducer sheath 801 until a desired position is reached. Desired positioning of the anchor shaft 811 within the patient may be determined by observing the position of an indicator on a portion of the system external to the patient, as shown in FIG. 15. Once within a vessel lumen 815, the un-deployed anchor 807 may then be deployed to a desired configuration, as shown in FIG. 17E. The deployed anchor 807 may be moved into contact with an inner surface 817 of the vessel wall 819, as shown in FIG. 17F. The anchor device 807 and the distal end of roll 809 are preferably positioned relative to one another such that, when deployed anchor device 807 is in contact with an inner surface 817 of the vessel wall 819, the roll 809 preferably is located outside vessel lumen 815, as shown in FIG. 17F.

The introducer 801 may then be withdrawn from the vessel lumen 815, and may then be removed completely or partially from the patient. FIG. 17G illustrates complete removal of the introducer shaft 801 from the patient. After removal of the introducer sheath 801 from at least the vessel lumen 815, the distal end of the roll 809 may remain within the tissue of the patient at a predetermined distance from the anchor device 807. A proximal end of the roll 809 may be located outside of the patient.

A distal end of the introducer 801 may be used to open a proximal end of the roll 809 by inserting the distal end of the introducer within the proximal end of the roll 809. This may force open the proximal end of the roll 809 to allow the heating element 821 to enter the roll 809.

A heating element 821 on a heating element shaft 823 may be passed over the anchor shaft 811 in an over-the-wire configuration, as shown in FIG. 17H The heating element 821 may have a diameter of approximately 4.5 mm. The heating element shaft may be about 40 to about 100 mm in length. The heating element 821 may be coupled to a handheld control unit 825. The heating element 821 may preferably be a flattened sphere, dome-shaped or any other suitable shape. Since the heating element 821 may be generally spherical, there may be three symmetrical axes. The shape of the heating element 821 preferably allows for accurate positioning of the heating element 821 both over a puncture site in a vessel wall and above the anchor device 807.

The heating element 821 may be inserted into an open proximal end 827 of the roll 809, as shown in FIG. 17J. The heating element 821 may be moved along the anchor shaft 811 toward the vessel 805, as shown in FIG. 17I. The heating element shaft 823 may be pushed toward the vessel 805 to move the heating element 821 against or near an outer surface of the vessel 805 near or in contact with a puncture. The roll 809 may open or expand gradually as the heating element 821 passes through the roll 809 to allow the heating element 821 to slide through the tissue to a desired position. The roll 809 may open to accommodate the heating element 821 near the heating element as the heating element 821 passes through the roll 809 towards the distal end of the roll 809.

The heating element 821 may move through the roll 809 into a desired position near the vessel wall 819 opposite the expanded anchor 807, as shown in FIG. 17K. The roll 809 may prevent the heating element 821 from being inserted into the vessel lumen 815 because the roll 809 may be coupled to the anchor shaft 811 outside of the vessel lumen 815. The coupling prevents the heating element 821 from entering the vessel lumen 815 because the heating element 821 may not pass the coupling point. The roll 809 may assist movement of the heating element 821 through tissue.

Optionally, a guide wire 808, shown in FIG. 17K, may be inserted into the vessel lumen along with the anchor shaft 811. The guide wire 8008 may be of a small diameter and may remain in the vessel lumen 815 after withdrawal of the anchor 807. The guide wire 808 may allow for an additional measure of positioning for the heating element 821 after the anchor 807 is removed from the vessel lumen 815. The guide wire 808 may be removed prior to a second heating stage. Alternatively, the guide wire 808 may be left in place until after a second heating stage to further ensure correct positioning of the heating element 821 during the second heating stage. The small diameter of the guide wire 808 may minimize damage to tissue during removal and may leave only a small opening in the vessel wall after removal.

The roll 809 may then be retracted from the patient as shown in FIG. 17L. A locking mechanism may prevent further movement of the heating element 821 after removal of the roll 809. An operator may apply pressure to a proximal end of the roll 809 in a direction towards a proximal end of the anchor shaft 811 to decouple the roll 809 from the anchor shaft 811 and remove the roll 809 from the patient. The roll 809 may be coupled to the anchor shaft 811 with adhesive that is strong enough to hold the roll 809 in place during positioning of the anchor shaft 811 and the roll 809 in the patient and during insertion and positioning the heating element 821, but weak enough to allow detachment when desired, such as after the heating element 821 is correctly positioned.

Alternatively, the heating element 821 may decouple the roll 809 from the anchor shaft 811 when the heating element 821 reaches a desired position by putting pressure on the connection point between the anchor shaft 811 and the roll 809. The heating element 821 may pass through the coupling point between the anchor shaft 821 and the roll 809 to break the adhesive or other bond and thereby detach the roll 809 from the anchor shaft 821. In alternative embodiments, the roll 809 may be left within the patient during the heating stages.

Once positioned, the heating element 821 may be in direct contact with the vessel wall or may be in close proximity. Preferably, the heating element 821 is in contact with or a predetermined distance from the vessel wall, but does not enter the vessel lumen. The anchor device 807 and the heating element 821 may sandwich the vessel wall and any intervening tissue between them. Any intervening tissue may be compressed between the anchor device 807 and the heating element 821. For example, approximately 1 mm may separate the anchor device 807 and the heating element 821. A locking point or a manual indication external to the patient may ensure determination and/or maintenance of the proper distance between the anchor device 807 and the heating element 821.

A first amount of heat may be applied to the vessel wall by the heating element 821. Heat may be applied in a duration and/or temperature sufficient to cause the heating element to "stick" temporarily to the vessel wall and/or intervening tissue, but not sufficient to close a puncture in the vessel wall. The heating element may have a non-stick coating, such as silicone, TEFLON, etc., to prevent permanent adhering of the vessel wall and/or intervening tissue to the heating element. Silicone is a preferred coating. The first amount of heat may allow the heating element to remain in position without the anchor device. The first amount of heat may shrink the puncture from approximately 2.7 mm, which is approximately the diameter of the introducer shaft, to approximately 1 mm, which is approximately the diameter of the anchor shaft.

After the application of the first amount of heat, the anchor device 807 may be transferred from the deployed position to the un-deployed position, as shown in FIG. 17M The anchor device 807 may then be withdrawn by withdrawing the anchor shaft 811, as shown in FIG. 17N.

After removal of the anchor device 807, a second duration and/or temperature of heat may be applied to the vessel wall and/or intervening tissue by the heating element to close the puncture. The second amount of heat may cause shrinking of the vessel wall and/or intervening tissue such that the puncture is completely or nearly completely closed.

After the second heating step is complete, the heating element shaft may be withdrawn from the patient. The heating element may be uncoupled from the tissue by application of a twisting force on the heating element shaft. The coating on the heating element should be chosen and applied such that the coating allows temporary sticking of the heating element, but not permanent bonding of the heating element thereto. If the guide wire 808 was left within the vessel until after the second heating step, the guide wire 808 may then also be removed. The small diameter of the guide wire 808 may reduce any unwanted bleeding from the tissue caused by its removal.

Application of manual compression for a short period of time, such as approximately one minute, may be required after removal of the system to complete closing of the puncture site and stop any bleeding from the tissue. Any small opening left at the puncture site may be closed by manual compression. The procedure using the system described above may take approximately three minutes and may be followed by approximately one minute of manual compression.

Figure 18:
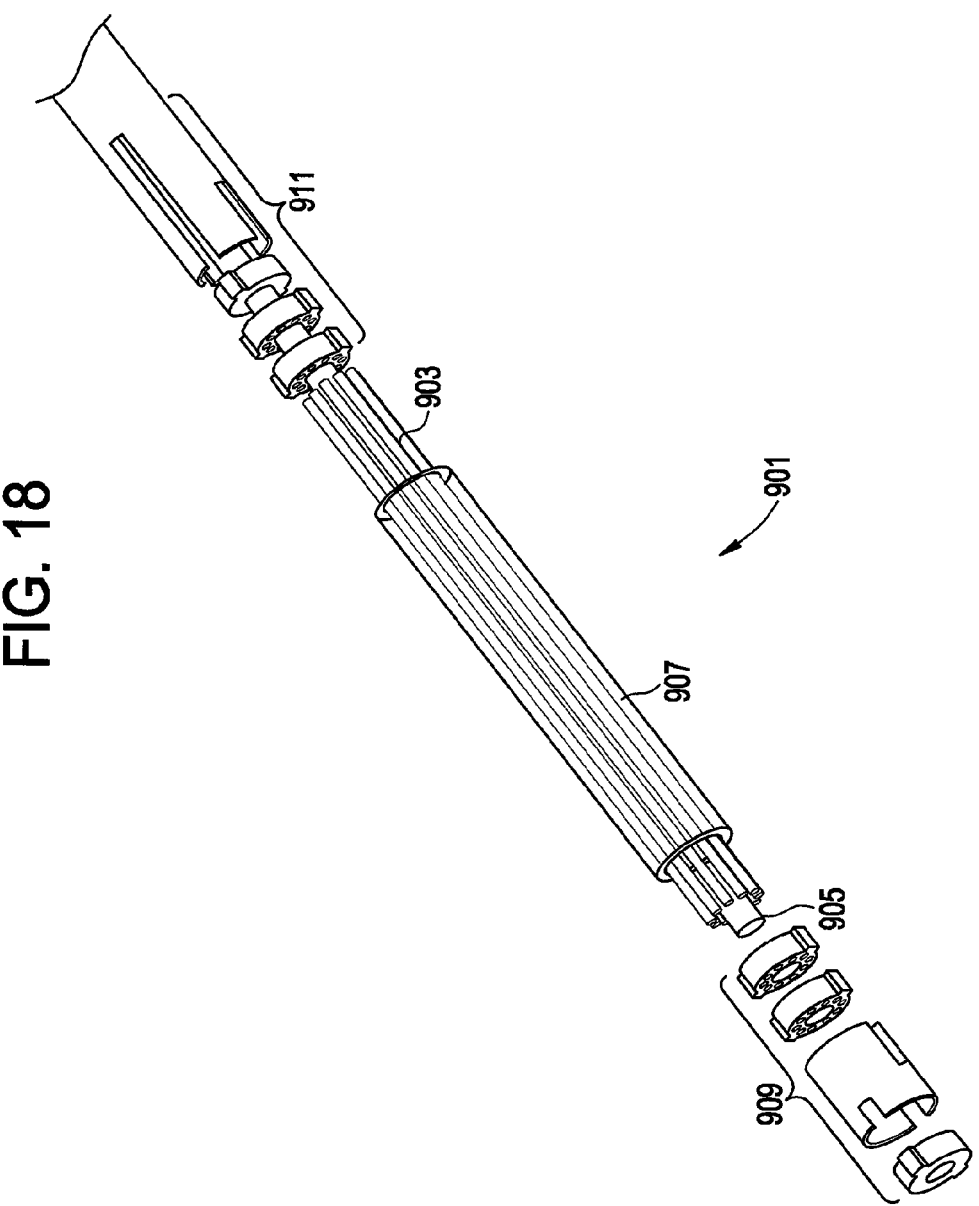
FIG. 18 illustrates an embodiment of an exploded view of an anchor distal end.

FIG. 18 is an exploded view of an anchor distal end 901. One or more expansible elements 903 may surround a central shaft 905. The one or more expansible elements 903 may initially be parallel to the central shaft 905. The one or more expansible elements 903 may be deformed by shape-memory, mechanical activation or other mechanisms to a final position. A coating 907 may cover the one or more expansible elements 903. The coating 907 may extend along the entire length of the one or more expansible elements 903, or a portion thereof. The one or more expansible elements 903 may be coupled at a distal end to the central shaft 905 by a series of distal couplers 909. The one or more expansible elements may be coupled at a proximal end to the central shaft 905 by one or more proximal couplers 911.

Figure 19A:
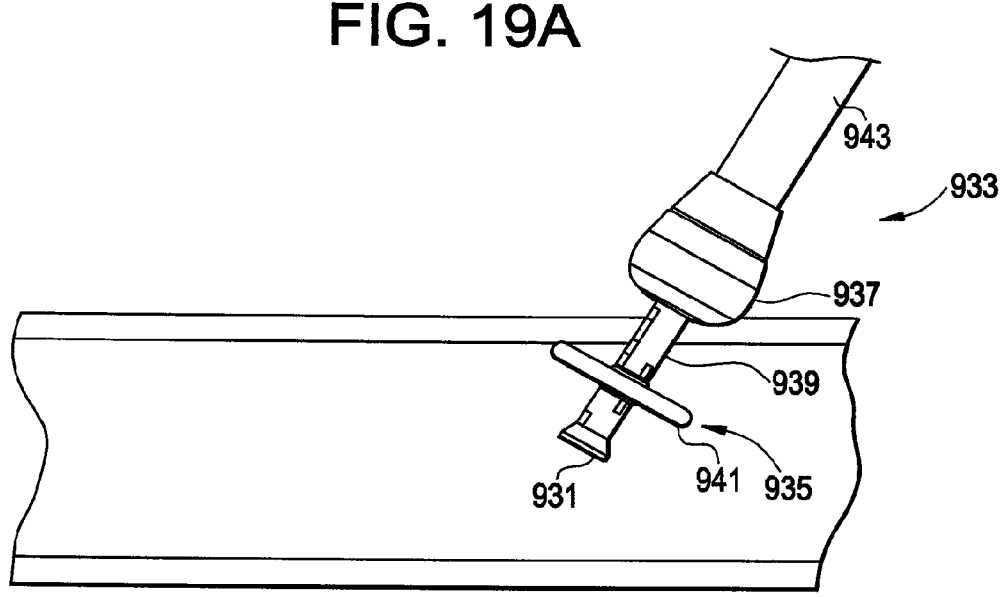
FIGS. 19A-19C illustrate an embodiment of a large tip anchor on an apparatus.
Figure 19B:
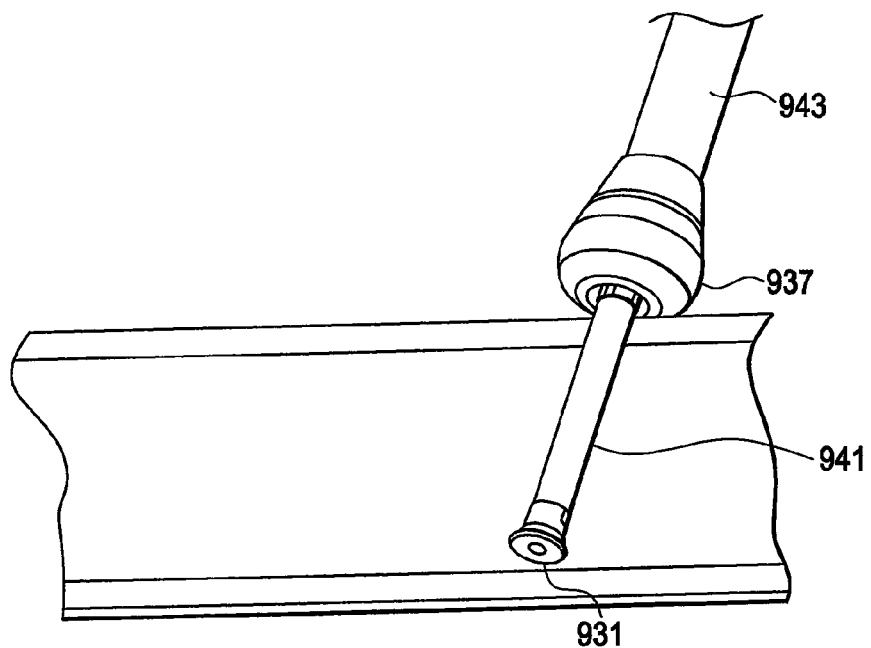
Figure 19C:
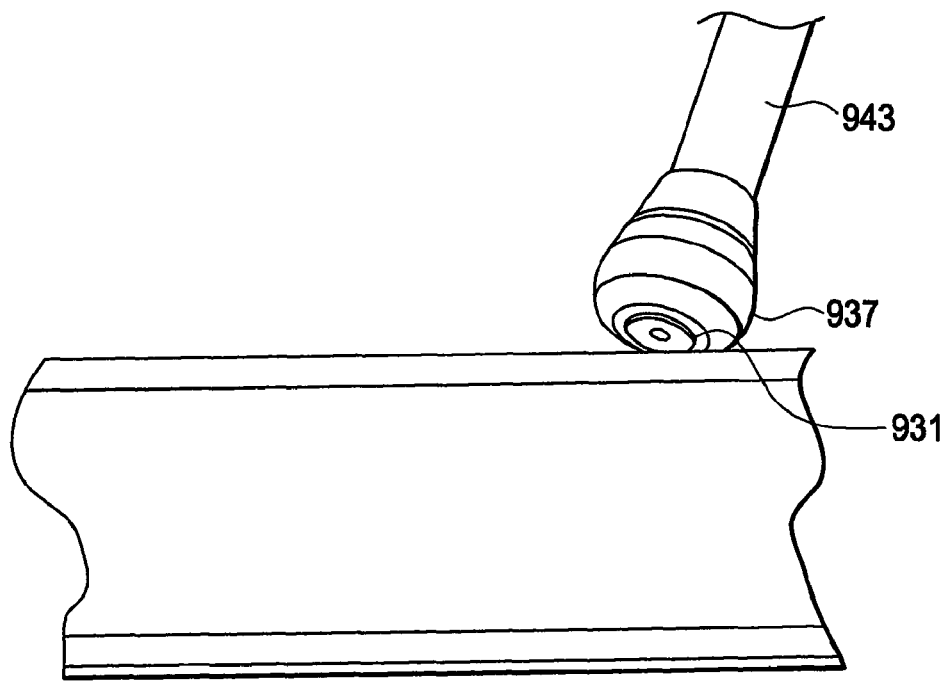

FIGS. 19A-19C show a large tip 931 on an anchor device 935 of a system 933 for closing a puncture in a vessel wall The large tip 931 is intended only to refer to the relative dimension of the tip in relation to tips in other embodiments of the present invention. A lumen may exist in a heating element 937 for passing the heating element 937 over an anchor shaft 939. In a preferred embodiment, the large tip 931 may have a diameter of approximately 2 mm if the lumen in the heating element 937 is approximately 1.3 mm. The lumen of the heating element 937 may be approximately 1.0-1.3 mm. An anchor shaft 939 may have a slightly smaller diameter than the lumen of the heating element 937. The system 933 operates similarly to the previously described embodiments. A heating element 937 on a heating element shaft 943 may be inserted over the anchor shaft 939 opposite a deployed anchor device 941, as shown in FIG. 19A. After an initial application of heat, the anchor device 941 may be compressed or un-deployed. The large tip 931 may have a circumference larger than the compressed circumference of the anchor device 941, as shown in FIG. 19B. The anchor 941 may be withdrawn into the heating element 937, as shown in FIG. 19C. The large tip 931 may sit flush with the distal end of the heating element 937. The anchor device 941 may not be completely removed from the patient until the heating element 937 is withdrawn and the anchor device 941 is withdrawn with the heating element 937. An angled opening of the lumen of the heating element 937 relative to the anchor shaft 939 may preferably be less than approximately 45 degrees to prevent unwanted sandwiching of tissue between the heating element 937 and the large tip 931. The anchor 941 may be removed from the vessel lumen and moved flush with the distal end of the heating element prior to heating, after an initial heating or at any other desired time.

Figure 20A:
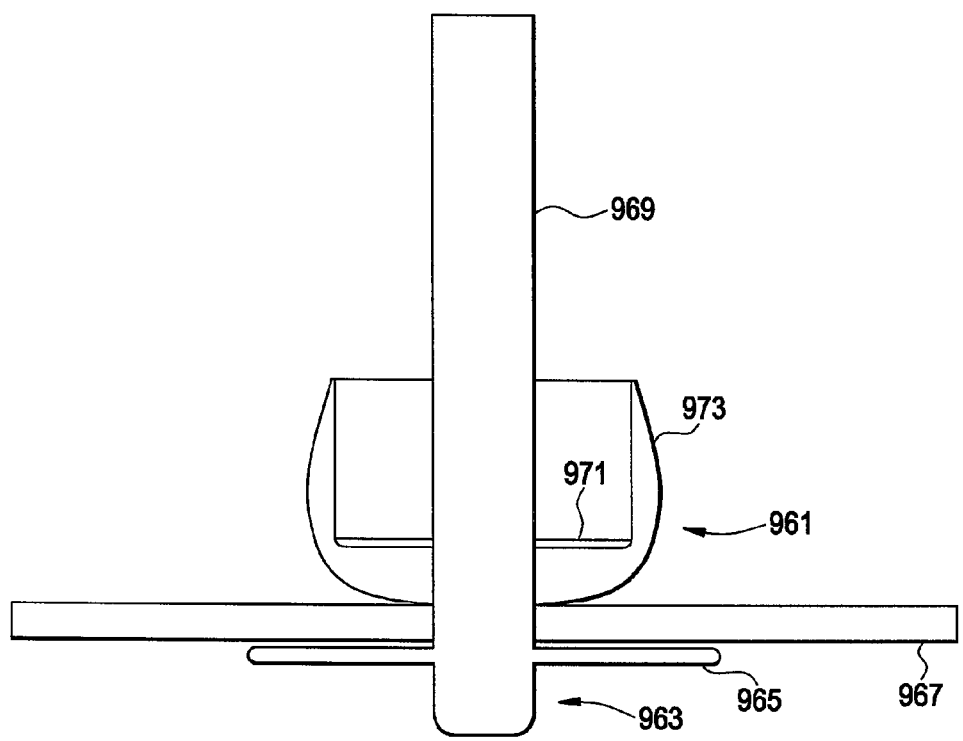
FIGS. 20A-20B illustrate an embodiment of a flattened dome heating element.
Figure 20B:
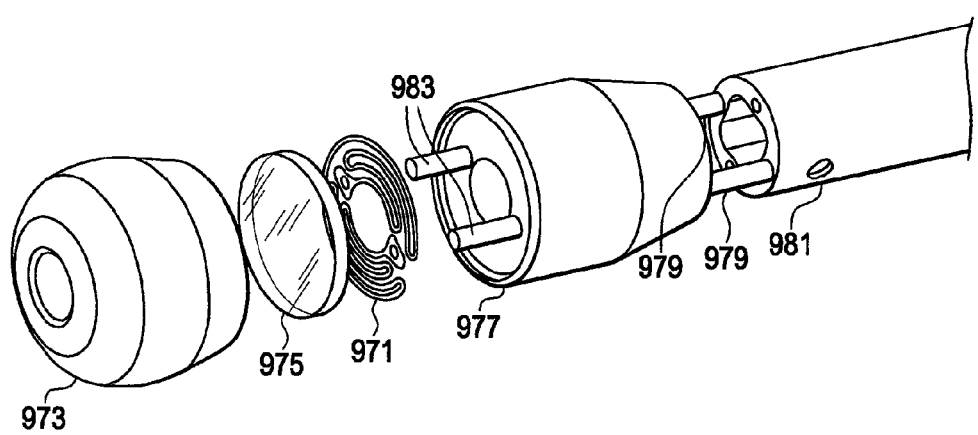

FIG. 20A is a cross section view of a heating element 961 and an anchor system 963. An anchor device 965 may be flush with a puncture in a vessel 967. The anchor system 963 may have an anchor shaft 969 passing through the heating element 961. A conducting element 971 may be disposed within a conducting dome 973. The conducting dome 973 may preferably be made of stainless steel or another suitable material. FIG. 20B is an exploded view of a heating element 961. A ceramic or other suitable adhesive 975 may couple the conducting element 971 to the conducting dome 973. A ceramic or other suitable connector 977 may be coupled to the conducting dome 973 and may sandwich the conducting element 971 and adhesive 975. Wires 979 may connect the connector 977 to a shaft 981. The wires 979 may preferably be copper-tin or another similar type of wire. Pegs 983 may preferably align the heating element 971 within the conducting dome 973.

Generally, embodiments of the present invention may close punctures in tissue by applying heat directly to or over a puncture site. Heating elements may produce heat by applying direct current over a metal heating element. This may allow only heat to transfer to the tissue, but not electric current, such as when using radiofrequency during electrocautery, light energy when using lasers or shock waves when using ultrasound.

Two mechanisms for heat flow inside a tissue are:

1. Conduction—meaning that the gradient in temperature within the tissue itself drives the flow.

2. Convection of thermal energy by the perfusing blood.

The heating element may be located just on top of the puncture site so the heat conduction is radial and gradually on the longitudinal and circumferential axis. Regarding the transverse axis, the rapid convection of thermal energy by the blood flow may protect the intima layer from excess thermal effects.

Whereas cauterizing effects of electrocautery and/or electrosurgery can achieve hemostasis by fusion of both sides of the artery and occlusion of the vessel, the present invention may use low voltage for a short time to generate approximately 70°-120° C. temperatures. The thermal effect of the heating element on the artery wall is shrinkage and closure of the puncture.

The main components of an artery wall are collagen and elastin. The collagen molecule is made up of three polypeptide chains, which are stabilized in a triple-helix arrangement by intra-molecular cross links. These molecules are, in turn, aggregated into a parallel pattern to form collagen fibrils. The fibril arrangement may be maintained by intermolecular cross-links and may provide the artery wall tissue with its tensile properties. Intra-molecular cross-links may be reducible covalent aldehyde bonds that are sensitive to heat. When collagen is heated, the heat-labile intra-molecular cross-links may be broken, while the heat-stable intermolecular bonds remain in tension. The collagen shrinkage may be the cumulative effect of the "unwinding" of the triple-helix due to these processes.

The general order of histological change reflected by the thermal effect of the present invention on the artery wall tissue is:

1. Swelling of collagen bands.
2. Thickening of the media layer.
3. Spotty hyalinization of collagen fibers within bands.
4. Increasing regional volumes of diffuse collagen hyalinization.

A preclinical study in accordance with principles of the present invention was performed on swine. An approximately 4.5 mm spherical heating element was applied to an approximately 6 Fr puncture. The preclinical study applied temperatures of 75° C. to 350° C. on top of the puncture made by a 6 Fr introducer for 10 seconds, and followed up with the swine for up to 6 weeks. The histopathology results demonstrate: minimal neointima, increase proteoglycans to a variable extent in the media and scarring of the adventitial without residual necrosis or inflammation. Elastic laminae were intact and no luminal thrombus was identified.

The following are results of testing of a heating element in accordance with principles of the present invention. There were no significant changes seen, other that platelet-lined arteriotomy sites and hemorrhage. At 72 hours, there were no intimal changes, and were no adventitial changes of necrosis of collagen and adventitial vasa vasorum. There was no obvious correlation between the degree of necrosis and temperature. Only one artery, which was exposed at 350° C. heat, showed medial, consisting of medial necrosis with increased proteoglycan, at 72 hours. At 10 days, minimal neointimal was present only in the femoral arteries; the carotid vessels did not exhibit intimal changes. There was minimal persistent necrosis of the adventitial vasa vasorum at 10 days, with inflammation and early fibrosis of the adventitial collagen. Medial changes consisted of regenerative changes with increased proteoglycans, without residual necrosis, and with occasional calcification in areas of puncture sites. At 42 days, there was scarring of the adventitial vasa vasorum without residual necrosis or inflammation. Minimal neointima was present again only in femoral arteries. Medial changes consisted of increased proteoglycans to a variable extent. At all time points, elastic laminae were intact and no luminal thrombus was identified. No particular dose response related effect was noted by quantization of parameters.

In another series of tests on swine, three of four vessels had heat treatment with an approximately 4.5 mm sphere over an approximately 6 Fr puncture. The perforation sites demonstrated fibrosis with healing, with foreign body granuloma in two. The intima demonstrated minimal thickening, to a maximal thickness of 0.33 mm, without stenosis or persistent non-endothelialized thrombus. The media demonstrated loss of smooth muscle cells and increased proteoglycans, with calcification in one of the three treated vessels. The change extended up to 22.5 mm in length. The internal and external elastic laminae were intact with the exception of at the perforation site. The adventitia demonstrated fibrosis, up to 7.5 mm in length. The control artery demonstrated changes consistent with perforation and healing. There were no significant untoward or unexpected complications or tissue effects from the treatment. The persistent changes at 42 days included minimal intimal thickening, medial smooth muscle cell loss, and adventitial fibrosis. The length of the treatment effect suggests that the heat disperses beyond the distance of the heating element itself, possibly due to heating of fluid in the anchor balloon.

Without wishing to be limited by mechanism of action, in a preferred embodiment only, there are three likely main mechanisms operating to close punctures in vessels treated by heating elements of the present invention:

1—Heat-induced fusion of loose periadventitial tissue.
2—Heat-induced clot formation.
3—Thermal shrinkage of collagen and elastin.

The following are assumptions for tissue response to heat:

1. Once the temperature reaches 43°-45° C., cells could die.
2. Any elevation in temperature will increase blood coagulation (in stasis).
3. Collagen denaturation initiates at approximately around 65° C., with maximal shrinkage effect approximately around 85° C.
4. Fusion of loose connective tissue requires a temperature of greater than 115° C.
5. Regarding time for which heat may be applied: At 43° C., changes may be reversible for 30-50 minutes; at 45° C. or greater, this time may shorten dramatically. Collagen shrinkage effect at 85° C. may reach maximal effect at 1-15 seconds. Connective tissue may burn and char within 1 second of contact with a probe tip at greater than 115° C.

The following are exemplary technical specifications for a heating element. These are only for illustrative purposes and other configurations and specifications may be used.

1. The orifice diameter of a 6 Fr introducer sheath used in many diagnostic and therapeutic procedures is approximately 2.7 mm (external size). Assuming no post-withdrawal contraction of tissue surrounding the puncture, and 1.15 mm overlap of the introducer sheath and the heating element—the heating element diameter may be approximately 5.0 mm Post-withdrawal contraction may reduce the necessary size of the heating element. Reduced overlap may also reduce the necessary size of the heating element. In general, the size of the heating element should be at least slightly larger than the puncture.

2. Heat production and conduction should preferably be nearly uniform over the entire surface area of the heating element.

3. The heating element may produce approximately 115° C. for approximately 15 seconds in a single cycle. The handheld unit may allow for determination of the heating temperature, duration and number of cycles. The handheld unit may have preferred combinations pre-programmed. The heating element may operate in one or more cycle of approximately 15 watts per cycle for approximately 5 seconds per cycle. Wattage may range from approximately 1 watt to approximately 25 watts per cycle. Duration of cycles may range from approximately 1 second to approximately 10 seconds. Preferably, two cycles may be used.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. An apparatus for closing a puncture in a vessel wall comprising:
    an anchor shaft having a distal end and a tip,
    an anchor disposed on the distal end of the anchor shaft, a distal end of the anchor is proximally spaced apart from the tip of the anchor shaft and adapted for being in a deployed position and un-deployed position, wherein the anchor is adapted for being in the deployed position within a vessel lumen and is further adapted for being moved into contact with an inner surface of a vessel wall, and
    an approximately dome-shaped heating element having a lumen and a distal opening for passing the heating element over the anchor shaft, wherein the tip of the anchor shaft is seated in the heating element upon retraction of the anchor shaft, the heating element adapted for being disposed outside the vessel wall, the heating element and the deployed anchor being adapted for disposing the vessel wall there between and wherein the heating element is capable of heating when the anchor is deployed and when the anchor is un-deployed.

2. The apparatus of claim 1, further comprising a trigger to lock a relative position of the heating element and the anchor.

3. The apparatus of claim 1, wherein the heating element is approximately spherical for positioning over the puncture in the vessel wall and above the anchor device.

4. The apparatus of claim 1, wherein the heating element includes a conducting dome and a conducting element disposed within the conducting dome.

5. The apparatus of claim 1, wherein the heating element comprises a metal conducting dome and a disc-shaped conducting element.

6. The apparatus of claim 1, wherein the heating element and the anchor are coaxially disposed and are positionable to compress the vessel wall therebetween.

7. The apparatus of claim 1, wherein the vessel wall and tissue are adapted to be sandwiched between the heating element and the deployed anchor.

8. The apparatus of claim 1, further comprising: a pass-through device at least partially surrounding the anchor shaft for facilitating passage of the heating element over the anchor shaft into proximity with the outer surface of the vessel wall opposite the anchor.

9. The apparatus of claim 1, wherein the anchor shaft has an anchor shaft circumference and the tip has a circumference larger than the anchor shaft circumference.

10. The apparatus of claim 1, wherein the heating element is a resistant heating element.

11. The apparatus of claim 1, wherein the tip of the anchor shaft has a diameter of approximately 2 mm and wherein a diameter of the lumen of the heating element is approximately 1.3 mm.

12. The apparatus of claim 1, wherein a diameter of the lumen of the heating element is approximately 1.0-1.3 mm.

13. The apparatus of claim 1, wherein the tip of the anchor shaft is seated in the heating element so it is prevented from being withdrawn from the patient until the heating element is withdrawn.

14. The apparatus of claim 1, wherein the distal opening of the heating element is angled and wherein the angled opening relative to the anchor shaft is less than 45 degrees.

15. The apparatus of claim 1, wherein the apparatus further comprises a guide wire.

16. The apparatus of claim 1, wherein the tip of the anchor shaft is flush with the distal end of the heating element.

* * * * *